(12) United States Patent
Molaei et al.

(10) Patent No.: US 9,089,332 B2
(45) Date of Patent: Jul. 28, 2015

(54) VASCULAR REMODELING DEVICE

(75) Inventors: Masoud Molaei, Mountain View, CA (US); Evan David Epstein, Costa Mesa, CA (US); Gabriel Francis Wilgus Newell, San Francisco, CA (US); Quang Tran, Redwood City, CA (US)

(73) Assignee: Covidien LP, Mansfield, MA (US)

( * ) Notice: Subject to any disclaimer, the term of this patent is extended or adjusted under 35 U.S.C. 154(b) by 163 days.

(21) Appl. No.: 13/428,237

(22) Filed: Mar. 23, 2012

(65) Prior Publication Data

US 2012/0245675 A1    Sep. 27, 2012

Related U.S. Application Data

(60) Provisional application No. 61/467,771, filed on Mar. 25, 2011, provisional application No. 61/487,648, filed on May 18, 2011.

(51) Int. Cl.
*A61M 29/00* (2006.01)
*A61B 17/12* (2006.01)
*A61B 17/00* (2006.01)

(52) U.S. Cl.
CPC ..... *A61B 17/12118* (2013.01); *A61B 17/12172* (2013.01); *A61B 2017/00526* (2013.01)

(58) Field of Classification Search
CPC ............ A61B 17/12113; A61B 17/12109; A61B 17/12172; A61B 17/0057; A61B 2017/00575; A61B 17/12118; A61B 2017/00526; A61F 2/82; A61F 2002/823; A61F 2002/825; A61F 2/01; A61F 2/013; A61F 2002/016; A61F 2002/018

USPC ........... 623/1.15, 1.16, 1.18, 1.3, 23.72, 1.13, 623/1.35, 1.2; 606/191, 200, 213, 215, 216
See application file for complete search history.

(56) References Cited

U.S. PATENT DOCUMENTS

| 4,425,908 A | 1/1984 | Simon |
|---|---|---|
| 4,619,246 A | 10/1986 | Molgaard-Nielsen et al. |

(Continued)

FOREIGN PATENT DOCUMENTS

| CA | 2607529 | 4/2008 |
|---|---|---|
| CN | 101472537 A | 7/2009 |

(Continued)

OTHER PUBLICATIONS

Hill, et al., "Initial Results of the AMPLATZER Vascular Plug in the Treatment of Congenital Heart Disease, Business Briefing," US Cardiology 2004.

(Continued)

*Primary Examiner* — Gregory Anderson
(74) *Attorney, Agent, or Firm* — Mark J. Kertz, Esq.

(57) ABSTRACT

A vascular remodeling device is provided. The device has an anchor portion, sized for deployment in a blood vessel, that is radially expandable from a collapsed state to an expanded state. The device also includes a distal portion sized for deployment in a blood vessel. The distal portion is radially expandable from a collapsed state to an expanded state and has a distal face that is sufficiently occlusive in the distal-to-proximal direction to perform a therapeutic blocking function in an aneurysm neck. The device also has an intermediate portion that interconnects a distal end of the anchor portion and a proximal end of the distal portion. In some embodiments, the anchor portion and/or distal portion has a plurality of interconnected struts.

42 Claims, 29 Drawing Sheets

(56) References Cited

U.S. PATENT DOCUMENTS

| | | |
|---|---|---|
| 4,655,771 A | 4/1987 | Wallsten |
| 4,768,507 A | 9/1988 | Fischell et al. |
| 4,921,484 A | 5/1990 | Hillstead |
| 4,998,539 A | 3/1991 | Delsanti |
| 5,026,377 A | 6/1991 | Burton et al. |
| 5,061,275 A | 10/1991 | Wallsten et al. |
| 5,064,435 A | 11/1991 | Porter |
| 5,104,404 A | 4/1992 | Wolff |
| 5,122,136 A | 6/1992 | Guglielmi et al. |
| 5,158,548 A | 10/1992 | Lau et al. |
| 5,222,971 A | 6/1993 | Willard et al. |
| 5,250,071 A | 10/1993 | Palermo |
| 5,334,210 A | 8/1994 | Gianturco |
| 5,378,239 A | 1/1995 | Termin et al. |
| 5,405,379 A | 4/1995 | Lane |
| 5,425,984 A | 6/1995 | Kennedy et al. |
| 5,484,444 A | 1/1996 | Braunschweiler et al. |
| 5,499,981 A | 3/1996 | Kordis |
| 5,527,338 A | 6/1996 | Purdy |
| 5,545,208 A | 8/1996 | Wolff et al. |
| 5,545,209 A | 8/1996 | Roberts et al. |
| 5,549,635 A | 8/1996 | Solar |
| 5,624,461 A | 4/1997 | Mariant |
| 5,634,942 A | 6/1997 | Chevillon et al. |
| 5,645,558 A | 7/1997 | Horton |
| 5,662,703 A | 9/1997 | Yurek et al. |
| 5,690,671 A | 11/1997 | McGurk et al. |
| 5,702,419 A | 12/1997 | Berry et al. |
| 5,713,907 A | 2/1998 | Hogendijk et al. |
| 5,725,552 A | 3/1998 | Kotula et al. |
| 5,728,906 A | 3/1998 | Eguchi et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,749,920 A | 5/1998 | Quiachon et al. |
| 5,766,151 A | 6/1998 | Valley et al. |
| 5,814,062 A | 9/1998 | Sepetka et al. |
| 5,830,230 A | 11/1998 | Berryman et al. |
| 5,846,261 A | 12/1998 | Kotula et al. |
| 5,855,578 A | 1/1999 | Guglielmi et al. |
| 5,879,366 A | 3/1999 | Shaw et al. |
| 5,911,731 A | 6/1999 | Pham et al. |
| 5,916,235 A | 6/1999 | Guglielmi |
| 5,925,060 A | 7/1999 | Forber |
| 5,928,228 A | 7/1999 | Kordis et al. |
| 5,928,260 A | 7/1999 | Chin et al. |
| 5,935,148 A | 8/1999 | Villar et al. |
| 5,935,362 A | 8/1999 | Petrick |
| 5,941,249 A | 8/1999 | Maynard |
| 5,944,738 A | 8/1999 | Amplatz et al. |
| 5,951,599 A | 9/1999 | McCrory |
| 5,957,948 A | 9/1999 | Mariant |
| 5,980,554 A | 11/1999 | Lenker et al. |
| 6,010,517 A | 1/2000 | Baccaro |
| 6,024,756 A | 2/2000 | Huebsch et al. |
| 6,033,423 A | 3/2000 | Ken et al. |
| 6,036,720 A | 3/2000 | Abrams et al. |
| 6,059,813 A | 5/2000 | Vrba et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,096,034 A | 8/2000 | Kupiecki et al. |
| 6,096,073 A | 8/2000 | Webster et al. |
| 6,099,526 A | 8/2000 | Whayne et al. |
| 6,106,530 A | 8/2000 | Harada |
| 6,123,715 A | 9/2000 | Amplatz |
| 6,139,564 A | 10/2000 | Teoh |
| 6,152,144 A | 11/2000 | Lesh et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,495 B1 | 2/2001 | Lenker et al. |
| 6,190,402 B1 | 2/2001 | Horton et al. |
| 6,193,708 B1 | 2/2001 | Ken et al. |
| 6,221,086 B1 | 4/2001 | Forber |
| 6,261,305 B1 | 7/2001 | Marotta et al. |
| 6,280,412 B1 | 8/2001 | Pederson, Jr. et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,332,576 B1 | 12/2001 | Colley et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,361,558 B1 | 3/2002 | Hieshima et al. |
| 6,368,339 B1 | 4/2002 | Amplatz |
| 6,375,668 B1 | 4/2002 | Gifford et al. |
| 6,383,174 B1 | 5/2002 | Eder |
| 6,391,037 B1 | 5/2002 | Greenhalgh |
| 6,409,750 B1 | 6/2002 | Hyodoh et al. |
| 6,428,558 B1 | 8/2002 | Jones et al. |
| 6,443,972 B1 * | 9/2002 | Bosma et al. .................. 606/200 |
| 6,447,531 B1 | 9/2002 | Amplatz |
| 6,454,780 B1 | 9/2002 | Wallace |
| 6,506,204 B2 | 1/2003 | Mazzocchi |
| 6,511,468 B1 | 1/2003 | Cragg et al. |
| 6,530,934 B1 | 3/2003 | Jacobsen et al. |
| 6,544,278 B1 | 4/2003 | Vrba et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,302 B2 | 6/2003 | Duerig et al. |
| 6,579,303 B2 | 6/2003 | Amplatz |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,592,605 B2 | 7/2003 | Lenker et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,551 B1 | 8/2003 | Sullivan et al. |
| 6,613,074 B1 | 9/2003 | Mitelberg et al. |
| 6,626,939 B1 | 9/2003 | Burnside et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,652,555 B1 | 11/2003 | VanTassel et al. |
| 6,652,556 B1 | 11/2003 | VanTassel et al. |
| 6,666,882 B1 | 12/2003 | Bose et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,682,505 B2 | 1/2004 | Bates et al. |
| 6,682,546 B2 | 1/2004 | Amplatz |
| 6,689,150 B1 | 2/2004 | VanTassel et al. |
| 6,689,486 B2 | 2/2004 | Ho et al. |
| 6,695,876 B1 | 2/2004 | Marotta et al. |
| 6,698,877 B2 | 3/2004 | Urlaub et al. |
| 6,699,274 B2 | 3/2004 | Stinson |
| 6,712,835 B2 | 3/2004 | Mazzocchi et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,792,979 B2 | 9/2004 | Konya et al. |
| 6,797,083 B2 | 9/2004 | Peterson |
| 6,802,851 B2 | 10/2004 | Jones et al. |
| RE38,653 E | 11/2004 | Igaki et al. |
| 6,811,560 B2 | 11/2004 | Jones et al. |
| 6,855,153 B2 | 2/2005 | Saadat |
| 6,855,154 B2 | 2/2005 | Abdel-Gawwad |
| RE38,711 E | 3/2005 | Igaki et al. |
| 6,860,893 B2 | 3/2005 | Wallace et al. |

(56) References Cited

U.S. PATENT DOCUMENTS

| | | |
|---|---|---|
| 6,936,055 B1 | 8/2005 | Ken et al. |
| 6,949,103 B2 | 9/2005 | Mazzocchi et al. |
| 6,949,113 B2 | 9/2005 | Van Tassel et al. |
| 6,953,472 B2 | 10/2005 | Palmer et al. |
| 6,979,341 B2 | 12/2005 | Scribner et al. |
| 6,989,019 B2 | 1/2006 | Mazzocchi et al. |
| 6,994,092 B2 | 2/2006 | van der Burg et al. |
| 6,994,717 B2 | 2/2006 | Konya et al. |
| 7,011,671 B2 | 3/2006 | Welch |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,063,679 B2 | 6/2006 | Maguire et al. |
| 7,070,607 B2 | 7/2006 | Murayama et al. |
| 7,070,609 B2 | 7/2006 | West |
| 7,083,632 B2 | 8/2006 | Avellanet et al. |
| 7,128,073 B1 | 10/2006 | van der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,244,267 B2 | 7/2007 | Huter et al. |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,393,358 B2 | 7/2008 | Malewicz |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,597,704 B2 | 10/2009 | Frazier et al. |
| 7,608,088 B2 | 10/2009 | Jones et al. |
| 7,621,928 B2 | 11/2009 | Thramann et al. |
| 7,632,296 B2 | 12/2009 | Malewicz |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,016,869 B2 | 9/2011 | Nikolchev |
| 8,016,872 B2 | 9/2011 | Parker |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 8,454,681 B2 | 6/2013 | Holman et al. |
| 2001/0000797 A1 | 5/2001 | Mazzocchi |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0165572 A1 | 11/2002 | Saadat |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143286 A1 | 7/2004 | Johnson et al. |
| 2004/0153119 A1 | 8/2004 | Kusleika et al. |
| 2004/0162606 A1 | 8/2004 | Thompson |
| 2004/0172056 A1 | 9/2004 | Guterman et al. |
| 2004/0172121 A1 | 9/2004 | Eidenschink et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0043759 A1* | 2/2005 | Chanduszko ............... 606/213 |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2005/0288763 A1 | 12/2005 | Andreas et al. |
| 2006/0052816 A1 | 3/2006 | Bates et al. |
| 2006/0064151 A1 | 3/2006 | Guterman et al. |
| 2006/0074475 A1 | 4/2006 | Gumm |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0200221 A1 | 9/2006 | Malewicz |
| 2006/0206199 A1 | 9/2006 | Churchwell et al. |
| 2006/0206200 A1 | 9/2006 | Garcia et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0282152 A1 | 12/2006 | Beyerlein et al. |

(56) References Cited

U.S. PATENT DOCUMENTS

| | | |
|---|---|---|
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0050017 A1 | 3/2007 | Sims et al. |
| 2007/0088387 A1 | 4/2007 | Eskridge et al. |
| 2007/0093889 A1 | 4/2007 | Wu et al. |
| 2007/0100415 A1 | 5/2007 | Licata et al. |
| 2007/0106311 A1 | 5/2007 | Wallace et al. |
| 2007/0135826 A1 | 6/2007 | Zaver et al. |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0051705 A1 | 2/2008 | Von Oepen et al. |
| 2008/0058856 A1 | 3/2008 | Ramaiah et al. |
| 2008/0065141 A1 | 3/2008 | Holman et al. |
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0125848 A1 | 5/2008 | Kusleika et al. |
| 2008/0132989 A1 | 6/2008 | Snow et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0243226 A1 | 10/2008 | Fernandez et al. |
| 2008/0249562 A1 | 10/2008 | Cahill |
| 2008/0281350 A1 | 11/2008 | Sepetka et al. |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0143849 A1 | 6/2009 | Ozawa et al. |
| 2009/0143851 A1 | 6/2009 | Paul, Jr. |
| 2009/0198315 A1 | 8/2009 | Boudjemline |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0228093 A1 | 9/2009 | Taylor et al. |
| 2009/0259202 A1 | 10/2009 | Leeflang et al. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2010/0004726 A1 | 1/2010 | Hancock et al. |
| 2010/0004761 A1 | 1/2010 | Flanders et al. |
| 2010/0023048 A1 | 1/2010 | Mach |
| 2010/0023105 A1 | 1/2010 | Levy et al. |
| 2010/0030200 A1 | 2/2010 | Strauss et al. |
| 2010/0030220 A1 | 2/2010 | Truckai et al. |
| 2010/0042133 A1 | 2/2010 | Ramzipoor et al. |
| 2010/0069948 A1 | 3/2010 | Veznedaroglu et al. |
| 2010/0087908 A1 | 4/2010 | Hilaire et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0185271 A1 | 7/2010 | Zhang |
| 2010/0268260 A1 | 10/2010 | Riina et al. |
| 2010/0274276 A1 | 10/2010 | Chow et al. |
| 2010/0312270 A1* | 12/2010 | McGuckin et al. ........... 606/200 |
| 2010/0331948 A1 | 12/2010 | Turovskiy et al. |
| 2011/0022149 A1 | 1/2011 | Cox et al. |
| 2011/0082493 A1 | 4/2011 | Samson et al. |
| 2011/0106234 A1 | 5/2011 | Grandt |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0276120 A1 | 11/2011 | Gilson et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0065720 A1 | 3/2012 | Strauss et al. |
| 2012/0101561 A1 | 4/2012 | Porter |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0245674 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0018451 A1 | 1/2013 | Grabowski et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304179 A1 | 11/2013 | Bialas et al. |
| 2014/0005713 A1 | 1/2014 | Bowman |

FOREIGN PATENT DOCUMENTS

| | | |
|---|---|---|
| DE | 102008028308 | 4/2009 |
| EP | 775470 | 5/1997 |
| EP | 855170 A2 | 7/1998 |
| EP | 1621148 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003520103 A | 7/2003 |

(56) References Cited

FOREIGN PATENT DOCUMENTS

| | | | |
|---|---|---|---|
| JP | 2003-524434 A | | 8/2003 |
| JP | 2004-049585 A | | 2/2004 |
| JP | 2005-522266 A | | 7/2005 |
| JP | 2006-506201 A | | 2/2006 |
| JP | 2008-541832 A | | 11/2008 |
| JP | 4673987 B2 | | 4/2011 |
| WO | WO-88/00813 | | 2/1988 |
| WO | WO-96/01591 | | 1/1996 |
| WO | WO-97/26939 | | 7/1997 |
| WO | WO-99/03404 | | 1/1999 |
| WO | WO-99/05977 | | 2/1999 |
| WO | WO-99/08607 | | 2/1999 |
| WO | WO-99/08743 | | 2/1999 |
| WO | WO-99/62432 | | 12/1999 |
| WO | WO-01/93782 | | 12/2001 |
| WO | WO-02/00139 | | 1/2002 |
| WO | WO 0200139 A1 * | | 1/2002 |
| WO | WO-02/071977 A2 | | 9/2002 |
| WO | WO-2005/117718 | | 12/2005 |
| WO | WO-2006/026744 | | 3/2006 |
| WO | WO-2006/034166 A2 | | 3/2006 |
| WO | WO-2006/052322 A2 | | 5/2006 |
| WO | WO-2006/091891 A2 | | 8/2006 |
| WO | WO-2006/119422 A2 | | 11/2006 |
| WO | WO-2007/047851 A2 | | 4/2007 |
| WO | WO-2007/076480 A2 | | 7/2007 |
| WO | WO-2007/121405 | | 10/2007 |
| WO | WO-2008/022327 A2 | | 2/2008 |
| WO | WO-2008/151204 | | 12/2008 |
| WO | WO-2008/151205 A2 | | 12/2008 |
| WO | WO-2008/157507 A2 | | 12/2008 |
| WO | WO-2009/076515 | | 6/2009 |
| WO | WO-2009/132045 A2 | | 10/2009 |
| WO | WO-2009/134337 | | 11/2009 |
| WO | WO-2009/135166 A2 | | 11/2009 |
| WO | WO-2010/028314 | | 3/2010 |
| WO | WO-2010/030991 | | 3/2010 |
| WO | WO-2011/057002 A2 | | 5/2011 |
| WO | WO-2011/057277 A2 | | 5/2011 |
| WO | WO-2011/130081 | | 10/2011 |
| WO | WO-2011/153304 | | 12/2011 |
| WO | WO-2012/112749 A2 | | 8/2012 |

OTHER PUBLICATIONS

Ronnen, "AMPLATZER Vascular Plug Case Study, Closure of Arteriovenous Fistula Between Deep Femoral Artery and Superficial Femoral Vein," AGA Medical Corporation, May 2007.

U.S. Appl. No. 13/629,678, filed Sep. 28, 2012.

Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

U.S. Appl. No. 13/669,652, filed Nov. 6, 2012.

U.S. Appl. No. 13/826,298, filed Mar. 14, 2013.

U.S. Appl. No. 13/795,556, filed Mar. 12, 2013.

U.S. Appl. No. 13/962,267, filed Aug. 8, 2013.

* cited by examiner

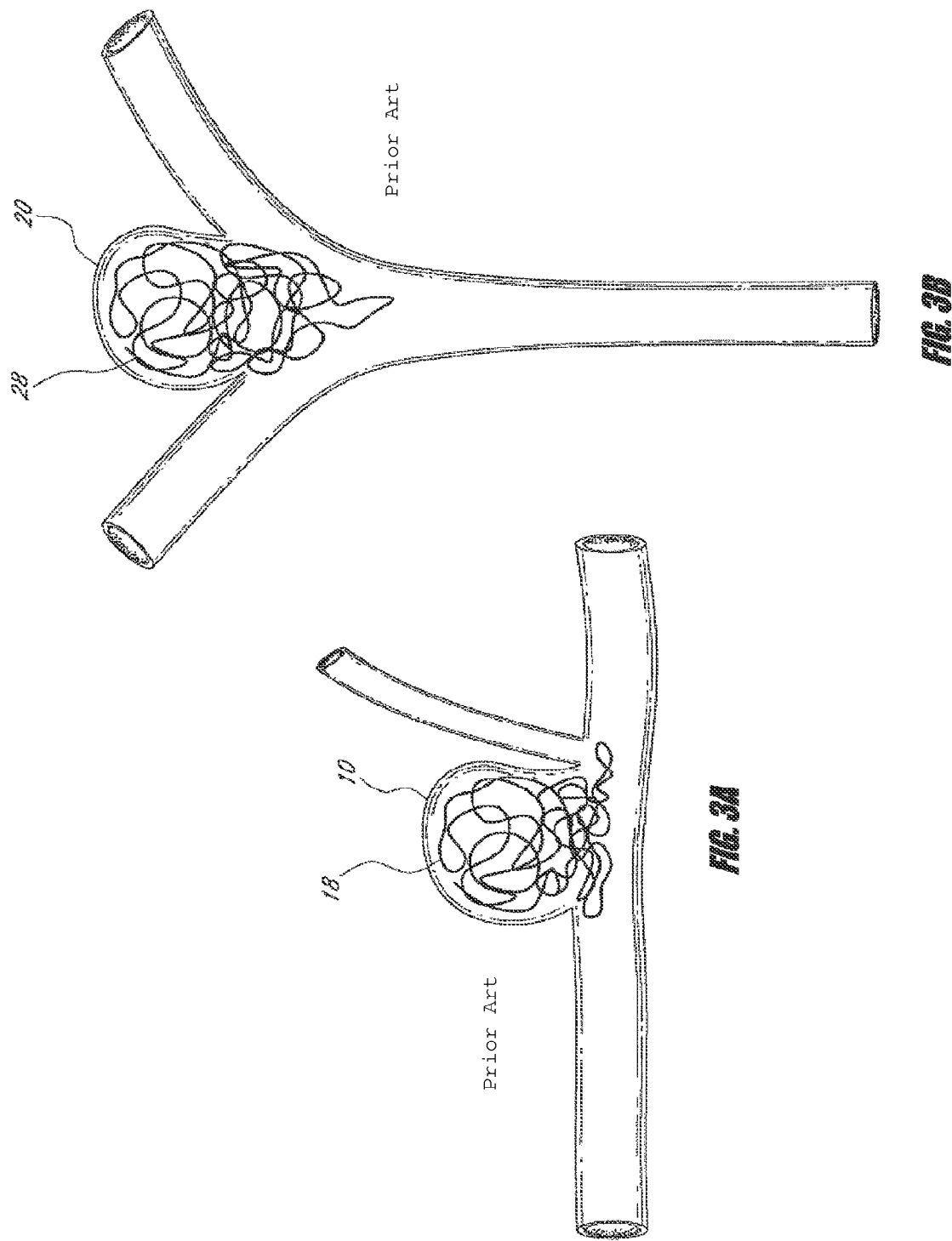

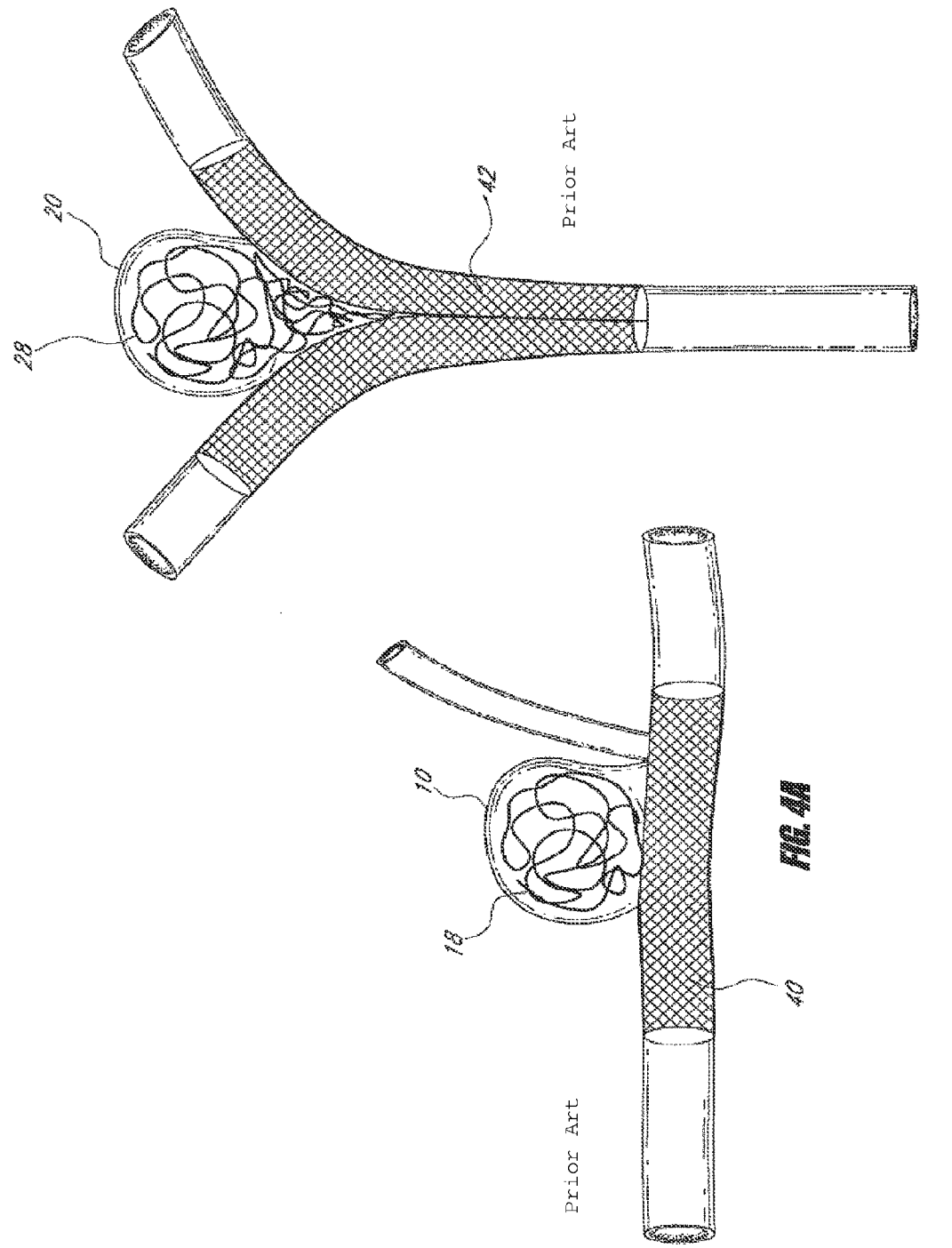

VASCULAR REMODELING DEVICE

This application claims priority, pursuant to 35 U.S.C. §119, to U.S. Provisional Patent Application No. 61/467,771, filed Mar. 25, 2011, titled VASCULAR REMODELING DEVICE, and to U.S. Provisional Patent Application No. 61/487,648, filed May 18, 2011, titled VASCULAR REMODELING DEVICE, the entire contents of which are incorporated herein by reference.

FIELD

The present application generally relates to vascular remodeling devices and to the manner of their positioning in vessels, including their positioning at the junction of neurovascular bifurcations having an aneurysm, and the use of such devices to treat an aneurysm.

BACKGROUND

Neurovascular or cerebral aneurysms affect about 5% of the population. Aneurysms may be located, for example, along arterial side walls (e.g., the aneurysm 10 illustrated in FIG. 1) and at arterial bifurcations (e.g., the aneurysm 20 illustrated in FIG. 2). The direction of fluid flow is generally indicated by the arrows 16, 26. The aneurysms 10, 20 each have a fundus 12, 22, a neck 14, 24, and a fundus-to-neck ratio or "neck ratio." If the neck ratio is greater than 2 to 1 or if the neck 14, 24 is less than 4 mm, the aneurysm 10, 20 may be treated with embolization coils alone because the coils will generally constrain themselves within the aneurysm 10, 20 without herniating into parent vessels. If the neck ratio is less than 2 to 1 or if the neck 14, 24 is greater than 4 mm, the aneurysms 10, 20 may be difficult to treat with embolization coils alone because the coils may be prone to herniating into parent vessels, as illustrated in FIGS. 3A and 3B. Herniation of coils may cause arterial occlusion, stroke, and/or death. Compared to the bifurcation illustrated in FIG. 2, the efferent vessels of the bifurcation may be at substantially different angles, have substantially different sizes, and/or be a different quantity (e.g., three or more). Compared to the bifurcation illustrated in FIG. 2, the aneurysm 20 of the bifurcation may be offset with respect to the junction (e.g., having a neck substantially open to one efferent vessel), tilted with respect to a plane created by the vessels (e.g., into or out of the page), etc. Each of these would still be accurately characterized as a "bifurcation" herein.

In order to inhibit such herniation, tubular neck remodeling devices, for example Neuroform®, available from Boston Scientific, and Enterprise™, available from Cordis Neurovascular, may be used to keep coils or other materials within the fundus of the aneurysm and out of the vessels. Tubular remodeling devices generally consist of a braided wire or cut metallic stent or stents covering the neck of the aneurysm. As illustrated in FIG. 4A, tubular remodeling devices 40 are generally useful for side wall aneurysms 10. As illustrated in FIGS. 4B and 4C, tubular remodeling devices 42, 44 are generally less useful for aneurysms 20 at bifurcations (e.g., the basilar tip area), for example because positioning/shaping the remodeling devices to preserve blood flow through the afferent and efferent vessels while also inhibiting herniation of coils 28 out of the aneurysm 20 can be difficult.

SUMMARY

The present disclosure includes, without limitation, the following embodiments. Various embodiments of the subject technology are described as numbered clauses (1, 2, 3, etc.) for convenience. These are provided as examples, and do not limit the subject technology or the present disclosure. It is noted that any of the dependent clauses may be combined in any combination, and placed into a respective independent clause. The other clauses can be presented in a similar manner.

1. A vascular remodeling device, comprising:
    an anchor portion radially expandable from a collapsed state to an expanded state in a blood vessel such that, when expanded, the anchor portion engages a wall of the vessel, the anchor portion having a longitudinal axis and a first waist comprising the radially largest region of the anchor portion in the expanded state;
    a distal portion radially expandable from a collapsed state to an expanded state in a blood vessel and having a second waist comprising the radially largest region of the distal portion in its expanded state, the distal portion having a distal face located distal to the second waist; and
    an intermediate portion that couples a distal end of the anchor portion and a proximal end of the distal portion at about the longitudinal axis, the intermediate portion comprising the radially narrowest region of the device between the first waist and the second waist, the distal portion being pivotable radially away from the longitudinal axis about the intermediate portion.

2. The device of clause 1, wherein the intermediate portion is confined within a radially central region of the device.

3. The device of clause 1, wherein the intermediate portion is radially narrower than the first waist and the second waist.

4. The device of clause 1, wherein the distal portion comprises a plurality of distal struts that extend longitudinally and radially outwardly toward the second waist.

5. The device of clause 4, wherein the distal struts extend longitudinally and radially outwardly from the intermediate portion toward the second waist, and further extend longitudinally and radially inwardly from the second waist toward a radially central region of the device.

6. The device of clause 4, wherein the distal struts each have a proximal end and a distal end, and the distal struts are not joined to each other along their lengths between their proximal and distal ends.

7. The device of clause 4, wherein the distal struts extend longitudinally and radially inwardly from the second waist to form the distal face of the distal portion.

8. The device of clause 7, wherein the distal struts forming the distal face of the distal portion have widened portions.

9. The device of clause 8, wherein the widened portions of the distal struts are wider than a width of distal struts forming a proximal face of the distal portion, the proximal face located proximal to the second waist.

10. The device of clause 8, wherein each of the widened portions of the distal struts further comprises a first and second ramp, wherein the first ramp extends from an edge of its respective strut to an edge of the widened portion, and the second ramp extends from the edge of the widened portion to the edge of the respective strut.

11. The device of clause 4, wherein the distal struts taper inwardly as they extend proximally from the second waist toward the intermediate portion.

12. The device of clause 4, wherein a proximal end of each distal strut is joined to the intermediate portion.

13. The device of clause 1, wherein the anchor portion comprises a plurality of anchor struts that extend longitudinally and radially outwardly toward the first waist and the distal portion comprises a plurality of distal struts that extend longitudinally and radially outward toward the second waist.

14. The device of clause 1, wherein the anchor portion and distal portion are able to pivot multiaxially relative to each other at or near the intermediate portion.

15. The device of clause 1, wherein the anchor portion, intermediate portion, and distal portion are formed from a single sheet or tube of material.

16. The device of clause 15, wherein the intermediate portion comprises an uncut portion of the single sheet or tube of material.

17. The device of clause 15, wherein the anchor portion and distal portion are able to pivot multiaxially relative to each other without plastic deformation of the intermediate portion.

18. The device of clause 1, wherein the distal face, when positioned adjacent an aneurysm, at least one of (a) supports a therapeutically effective amount and/or density of at least one filling material and/or device in the aneurysm, (b) promotes thrombogenesis, and (c) diverts flow from the aneurysm.

19. A vascular remodeling device, comprising:
an anchor portion sized for deployment in a blood vessel, the anchor portion radially expandable from a collapsed state to an expanded state such that, when expanded in a blood vessel, the anchor portion engages a wall of the vessel, the anchor portion having a longitudinal axis and a first waist comprising the radially largest region of the anchor portion when in the expanded state;
a distal portion sized and configured for deployment in a junction of two or more human blood vessels, the distal portion radially expandable from a collapsed state to an expanded state and having a second waist comprising the radially largest region of the distal portion when in the expanded state, the distal portion having a distal face, located distal to the second waist, sized and configured to occlude an aneurysm adjacent the junction when the second waist is in the junction and the distal portion is in the expanded state; and
an intermediate portion that interconnects a distal end of the anchor portion and a proximal end of the distal portion, the intermediate portion being the radially narrowest region of the device between the first waist and the second waist, the anchor portion and distal portion being able to pivot relative to each other at or near the intermediate portion.

20. The device of clause 19, wherein the intermediate portion comprises a radially central region of the device.

21. The device of clause 19, wherein the intermediate portion is radially narrower than the first waist and the second waist.

22. The device of clause 19, wherein the distal portion comprises a plurality of distal struts that extend radially outward toward the second waist.

23. The device of clause 22, wherein the distal struts extend distally away and radially outwardly from the intermediate portion toward the second waist, and further extend distally away and radially inwardly from the second waist toward a radially central region of the device.

24. The device of clause 22, wherein the distal struts each have a proximal end and a distal end, and the struts are not joined to each other anywhere along their length between their proximal and distal ends.

25. The device of clause 22, wherein the distal struts extend distally and radially inwardly from the second waist to form the distal face of the distal portion.

26. The device of clause 25, wherein the distal struts forming the distal face of the distal portion have widened portions, the widened portions configured to increase an occlusiveness of the distal face.

27. The device of clause 22, wherein the struts taper inward as they extend proximally from the second waist toward the intermediate portion.

28. The device of clause 22, wherein a proximal end of each strut is joined to the intermediate portion.

29. The device of clause 19, wherein the anchor portion comprises a plurality of anchor struts that extend radially outward toward the first waist and the distal portion comprises a plurality of distal struts that extend radially outward toward the second waist.

30. The device of clause 29, wherein the distal struts are independent of the anchor struts.

31. The device of clause 19, wherein the anchor portion and distal portion are able to pivot multiaxially relative to each other.

32. The device of clause 19, wherein:
the anchor portion forms a distal face located distal to the first waist;
the distal portion forms a proximal face located proximal to the second waist;
the distal face of the anchor portion tapers radially inward as it extends distally from the first waist to join the intermediate portion; and
the proximal face of the distal portion tapers radially inward as it extends proximally from the second waist to join the intermediate portion.

33. The device of clause 32, wherein the intermediate portion is confined in a radially central region of the device.

34. The device of clause 32, wherein the intermediate portion is radially narrower than the first waist and the second waist.

35. The device of clause 32, wherein the proximal face of the distal portion comprises a plurality of radially expandable distal struts and the distal face of the anchor portion comprises a plurality of radially expandable anchor struts.

36. The device of clause 35, wherein the intermediate portion, the anchor struts, and the distal struts are all formed from a single sheet or tube of material.

37. The device of clause 36, wherein the intermediate portion comprises an uncut portion of the single sheet or tube of material.

38. The device of clause 37, wherein the anchor portion and distal portion are able to pivot multiaxially relative to each other without plastic deformation of the intermediate portion.

39. The device of clause 19, wherein the anchor portion, intermediate portion, and distal portion are all formed from a single sheet or tube of material.

40. The device of clause 19, wherein:
the anchor portion forms a distal face located distal to the first waist;
the distal portion forms a proximal face located proximal to the second waist; and
both the distal face of the anchor portion and the proximal face of the distal portion are less occlusive than the distal face of the distal portion.

41. The device of clause 40, wherein the anchor portion forms a proximal face located proximal to the first waist, and the proximal face of the anchor portion is less occlusive than the distal face of the distal portion.

42. The device of clause 40, wherein the distal face of the anchor portion and the proximal face of the distal portion are configured not to impede blood flow significantly.

43. The device of clause 40, wherein the distal face of the distal portion is sufficiently occlusive in the distal-to-proximal direction to perform a therapeutic blocking function at the aneurysm.

44. The device of clause 19, wherein the distal face, when positioned adjacent the aneurysm, at least one (a) supports a therapeutically effective amount or density of aneurysm-filling materials or devices in an aneurysm, (b) promotes thrombogenesis, and (c) diverts flow.

45. A vascular remodeling device, comprising:
   an anchor portion comprising a plurality of anchor struts radially expandable from a collapsed state to an expanded state for engaging a wall of a blood vessel;
   a distal portion comprising distal struts radially expandable from a collapsed state to an expanded state for a engaging wall of a blood vessel, the distal struts forming a distal face; and
   an intermediate portion that connects a distal end of the anchor portion and a proximal end of the distal portion, the intermediate portion being radially narrower than the anchor portion and the distal portion;
   wherein at least one of a distal strut and an anchor strut is configured to flex along its length, allowing the distal portion to pivot multiaxially about the intermediate portion and relative to the anchor portion.

46. The device of clause 45, wherein the intermediate portion is radially narrower than the anchor portion and the distal portion.

47. The device of clause 45, wherein the distal struts extend longitudinally and radially outwardly from the intermediate portion to form a waist of the distal portion and extend distally from the waist to converge toward each other.

48. The device of clause 47, wherein the distal struts each have a proximal end and a distal end, and the struts are not joined to each other along their length between their proximal and distal ends.

49. The device of clause 47, wherein the distal struts extend longitudinally and radially inwardly from the waist to form the distal face of the distal portion.

50. The device of clause 49, wherein the distal struts forming the distal face of the distal portion have widened portions, the widened portions configured to increase an occlusiveness of the distal face.

51. The device of clause 50, wherein the widened portions of the distal struts are wider than a width of distal struts forming a proximal face of the distal portion, the proximal face located proximal to the second waist.

52. The device of clause 50, wherein the widened portions of the distal struts further comprise a first and second ramp, wherein the first ramp extends from an edge of the distal strut to an edge of the widened portion, and the second ramp extends from the edge of the widened portion to the edge of the distal strut.

53. The device of clause 47, wherein the distal struts taper inwardly as they extend proximally from the second waist toward the intermediate portion.

54. The device of clause 45, wherein the anchor portion, intermediate portion, and distal portion are all formed from a single sheet or tube of material.

55. The device of clause 54, wherein the intermediate portion comprises an uncut portion of the single sheet or tube of material.

56. The device of clause 55, wherein the anchor portion and distal portion are able to pivot multiaxially relative to each other without plastic deformation of the intermediate portion.

57. A method of treating an aneurysm located near a vascular bifurcation formed at a junction of a parent vessel and multiple branch vessels, the method comprising:
   providing a vascular remodeling device comprising an anchor portion, a distal portion, and an intermediate portion that couples the anchor portion to the distal portion;
   expanding an engagement region of the distal portion into engagement with a wall of the junction;
   orienting the distal portion relative to the aneurysm such that (a) the distal face extends distally from the engagement region, and tapers radially inwardly, toward the aneurysm, and (b) a proximal face of the distal portion extends proximally, and tapers radially inwardly, away from the aneurysm;
   tilting, about the intermediate portion, the distal portion relative to the anchor portion; and
   expanding an engagement region of the anchor portion into engagement with the parent vessel to inhibit movement of the distal portion from the junction.

58. The method of clause 57, further comprising leaving the distal portion in a tilted orientation relative to the anchor portion after expanding the engagement region of the distal portion.

59. The method of clause 57, further comprising inhibiting rotation of the distal portion with the expanded anchor portion.

60. The method of clause 57, further comprising allowing blood to flow from the parent vessel, through the anchor portion and the proximal face of the distal portion, and into the branch vessels.

61. The method of clause 60, wherein the anchor portion and the proximal face of the distal portion do not significantly inhibit blood flow.

62. The method of clause 57, further comprising supporting at least one filling material and/or device in the aneurysm with the distal face of the distal portion.

63. The method of clause 62, wherein the distal face of the distal portion comprises a plurality of struts, each strut having widened portions, the widened portions configured to increase an occlusiveness of the distal face.

64. The method of clause 57, further comprising maneuvering the device around a bend of a blood vessel, such that the distal portion and the anchor portion pivot relative to each other at or near the intermediate portion.

65. The method of clause 64, wherein the anchor portion comprises a group of anchor struts and the distal portion comprises a group of distal struts, the anchor struts and distal struts configured to flex at the bend.

66. The method of clause 64, wherein the intermediate portion allows the anchor portion and distal portion to pivot multiaxially relative to each other without substantial plastic deformation of the intermediate portion.

67. A vascular remodeling device, comprising:
   an anchor portion radially expandable from a collapsed state to an expanded state such that, when expanded in a blood vessel, the anchor portion engages a wall of the vessel, the anchor portion having a first waist comprising the radially largest region of the anchor portion when in the expanded state;
   a distal portion radially expandable from a collapsed state to an expanded state, the distal portion having a longitudinal axis and a second waist comprising the radially largest region of the distal portion when in the expanded state, the distal portion having a distal face located distal to the second waist; and an intermediate portion that couples a distal end of the anchor portion and a proximal end of the distal portion, the intermediate portion comprising the radially narrowest region of the device between the waists of the anchor and distal portions;

wherein the distal portion comprises a plurality of interconnected distal struts that extend distally from the proximal end of the distal portion such that (a) proximal to the second waist, the struts each (i) diverge from the longitudinal axis and (ii) divide into at least two struts; and (b) distal to the second waist, the struts each (i) merge with an adjacent strut, and (ii) converge toward the longitudinal axis.

68. The device of clause 67, wherein the interconnected distal struts are configured to maintain a three dimensional shape of the anchor portion.

69. The device of clause 67, wherein the interconnected distal struts are configured to prevent the struts from aggregating toward a single side of the blood vessel.

70. The device of clause 67, wherein the interconnected struts are configured to structurally supported each other.

71. The device of clause 67, wherein each strut extends from an origination junction and is divided into a first and second branch, wherein the first branch is connected to a first adjacent strut and the second branch is connected to a second adjacent strut.

72. The device of clause 71, wherein a length of the first branch and a length of the second branch are different.

73. The device of clause 71, wherein a length of the first branch and a length of the second branch are the same.

74. The device of clause 67, wherein at least one strut extends proximally from the intermediate portion and is divided into a first and second branch at or near the waist of the anchor portion, the first branch connected to a first adjacent strut and the second branch connected to a second adjacent strut.

75. The device of clause 74, wherein a length of the first branch and a length of the second branch are different.

76. The device of clause 74, wherein a length of the first branch and a length of the second branch are the same.

77. The device of clause 74, wherein the first and second adjacent struts extend proximally from the waist of the anchor portion toward a radially central region of the device.

78. The device of clause 67, wherein the distal struts extend longitudinally and radially inward from the waist of the distal portion to form the distal face of the distal portion.

79. The device of clause 78, wherein the struts forming the distal face have widened portions with increased cross-sectional widths that increase the occlusiveness of the distal face.

80. The device of clause 79, wherein the widened portions of the struts are each wider than a width of at least one of plurality of struts forming a distal portion proximal face, proximal to the waist of the distal portion.

81. The device of clause 79, wherein the widened portions of the struts further comprise a first and second ramp, wherein the first ramp extends from an edge of the strut to an edge of the widened portion, and the second ramp extends from the edge of the widened portion to the edge of the strut.

82. The device of clause 67, wherein the intermediate portion, the anchor portion, and the distal portion are all formed from a single sheet or tube of material.

83. The device of clause 67, wherein:
the anchor portion forms a distal face located distal to the waist of the anchor portion;
the distal portion forms a proximal face located proximal to the waist of the distal portion; and
both the distal face of the anchor portion and the proximal face of the distal portion are less occlusive than the distal face of the distal portion.

84. The device of clause 83, wherein the anchor portion forms a proximal face located proximal to the waist of the anchor portion, and the proximal face of the anchor portion is less occlusive than the distal face of the distal portion.

85. The device of clause 83, wherein the distal face of the anchor portion and the proximal face of the distal portion are configured such that they do not significantly impede blood flow.

86. The device of clause 67, wherein the distal face is configured to perform a therapeutic blocking function at an aneurysm, the function comprising at least one of (a) supporting maintenance of a therapeutically effective amount and/or density of at least one filling material and/or device in the aneurysm, (b) promoting thrombogenesis, and (c) diverting flow from the aneurysm.

87. A vascular remodeling device, comprising:
an anchor portion sized for deployment in a blood vessel, the anchor portion having a longitudinal axis and being radially expandable from a collapsed state to an expanded state, the anchor portion having a first waist comprising the radially largest region of the anchor portion when in the expanded state;
a distal portion sized and configured for deployment at a junction of two or more blood vessels;
the distal portion being radially expandable from a collapsed state to an expanded state, the distal portion comprising a second waist configured to engage a wall of the junction when the distal portion is in its expanded state, the second waist comprising the radially largest region of the distal portion when the distal portion is in its expanded state;
the distal portion comprising distal struts that form a distal face located distal to the second waist, the distal face configured to face an aneurysm adjacent the junction when the second waist engages the wall and the distal portion is in its expanded state; and
an intermediate portion that couples the anchor portion and the distal portion;
wherein the anchor portion comprises a plurality of interconnected distal struts that extend distally from the proximal end of the anchor portion such that (a) proximal to the first waist, the struts each (i) diverge from the longitudinal axis and (ii) divide into at least two struts; and (b) distal to the first waist, the struts each (i) merge with an adjacent strut, and (ii) converge toward the longitudinal axis.

88. The device of clause 87, wherein the distal face is configured to perform a therapeutic blocking function at the aneurysm, the function comprising at least one of (a) supporting maintenance of a therapeutically effective amount and/or density of at least one filling material and/or device in the aneurysm, (b) promoting thrombogenesis, and (c) diverting flow from the aneurysm.

89. The device of clause 87, wherein the interconnected struts are formed by a first plurality of struts extending from a proximal end of the anchor portion, and a second plurality of struts extending from the distal end of the anchor portion, the first and second plurality being interconnected at the first waist by a third plurality of sub-struts.

90. The device of clause 89, wherein the number of the first plurality of struts equals the number of the second plurality of struts.

91. The device of clause 89, wherein the number of the third plurality of sub-struts is double each of the number of the first plurality of struts and the number of the second plurality of struts.

92. The device of clause 87, wherein the interconnected struts are configured to maintain a three-dimensional shape of the anchor portion.

93. The device of clause 87, wherein the interconnected struts are configured to prevent the struts from moving substantially toward a side of the blood vessel.

94. The device of clause 87, wherein the interconnected struts are configured to support each other structurally.

95. The device of clause 87, wherein each strut has a proximal end, a distal end, and a center portion between the proximal and distal ends, each center portion being connected to adjacent struts.

96. The device of clause 87, wherein each strut extends from an origination junction and is divided into a first and second branch, wherein the first branch is connected to a first adjacent strut and the second branch is connected to a second adjacent strut.

97. The device of clause 96, wherein a length of the first branch and a length of the second branch are different.

98. The device of clause 96, wherein a length of the first branch and a length of the second branch are the same.

99. The device of clause 87, wherein at least one strut extends proximally from the intermediate portion and is divided into a first and second branch at or near the first waist, the first branch connected to a first adjacent strut and the second branch connected to a second adjacent strut.

100. The device of clause 99, wherein a length of the first branch and a length of the second branch are different.

101. The device of clause 99, wherein a length of the first branch and a length of the second branch are the same.

102. The device of clause 99, wherein the first and second adjacent struts extend proximally from the first waist toward a radially central region of the device.

103. The device of clause 87, wherein the distal portion comprises a plurality of interconnected distal struts, wherein the distal struts extend longitudinally and radially inward from the second waist to form the distal face of the distal portion.

104. The device of clause 103, wherein the struts forming the distal face of the distal portion have widened portions, the widened portions configured to increase the occlusiveness of the distal face.

105. The device of clause 104, wherein the widened portions of the struts are wider than a width of struts forming a proximal face of the distal portion, the proximal face located proximal of the waist of the distal portion.

106. The device of clause 104, wherein the widened portions of the struts further comprise a first and second ramp, wherein the first ramp extends from an edge of the strut to an edge of the widened portion, and the second ramp extends from the edge of the widened portion to the edge of the strut.

107. The device of clause 87, wherein the intermediate portion, the anchor portion and the distal portion are all formed from a single sheet or tube of material.

108. The device of clause 103, wherein the interconnected distal struts extend distally, from the proximal end of the distal portion, substantially along a distal portion longitudinal axis; and wherein proximal to the second waist, the struts (i) diverge from the longitudinal axis and (ii) each divide into at least two struts; and wherein distal to the second waist, the struts (i) merge with an adjacent strut, and (ii) converge toward the longitudinal axisl.

109. The device of clause 103, wherein the interconnected distal struts are configured to maintain a three dimensional shape of the distal portion.

110. The device of clause 108, wherein the interconnected distal struts are configured to prevent struts of the distal portion from moving substantially towards a side of the human blood vessel.

111. The device of clause 108, wherein the interconnected distal struts are configured to structurally support each other.

112. The device of clause 108, wherein each distal strut has a proximal end, a distal end, and a center portion between the proximal end and distal end, each center portion being connected to adjacent distal struts.

113. The device of clause 87, wherein each distal strut extends from an origination junction and is divided into a first and second branch, wherein the first branch is connected to a first adjacent distal strut and the second branch is connected to a second adjacent distal strut.

114. The device of clause 113, wherein a length of the first branch and a length of the second branch are different.

115. The device of clause 113, wherein a length of the first branch and a length of the second branch are substantially the same.

116. The device of clause 87, wherein at least one distal strut extends distally from the intermediate portion and is divided into a first and second branch at or near the second waist, the first branch connected to a first adjacent distal strut and the second branch connected to a second adjacent distal strut.

117. The device of clause 116, wherein a length of the first branch and a length of the second branch are different.

118. The device of clause 116, wherein a length of the first branch and a length of the second branch are the same.

119. The device of clause 116, wherein the first and second adjacent distal struts extend distally from the second waist toward a radially central region of the device.

120. The device of clause 87, wherein:
the anchor portion forms a distal face located distal to the first waist;
the distal portion forms a proximal face located proximal to the second waist; and
both the distal face of the anchor portion and the proximal face of the distal portion are less occlusive than is the distal face of the distal portion.

121. The device of clause 120, wherein the anchor portion forms a proximal face located proximal to the first waist, and the proximal face of the anchor portion is less occlusive than is the distal face of the distal portion.

122. The device of clause 120, wherein the distal face of the anchor portion and the proximal face of the distal portion are configured not to impede blood flow significantly.

123. The device of clause 120, wherein the distal face of the distal portion is sufficiently occlusive in the distal-to-proximal direction to perform a therapeutic blocking function at the aneurysm.

For purposes of summarizing the invention and the advantages that may be achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of this disclosure. These and other embodiments are presented in the following detailed description having reference to the attached figures, the disclosure not being limited to any particular disclosed embodiment(s).

BRIEF DESCRIPTION OF THE DRAWINGS

FIG. 3A illustrates an example embodiment of a side wall aneurysm with herniating embolization coils.

FIG. 3B illustrates an example embodiment of a bifurcation having an aneurysm with herniating embolization coils.

FIG. 4A illustrates an example embodiment of a side wall aneurysm treated with embolization coils and a tubular remodeling device.

FIGS. 4B and 4C illustrates example embodiments of a bifurcation having an aneurysm treated with embolization coils and tubular remodeling devices.

DETAILED DESCRIPTION

Although certain embodiments and examples are described below, it should be appreciated that this disclosure extends beyond the specifically disclosed embodiments and/or uses and obvious modifications and equivalents thereof. Thus, it is intended that the scope of this disclosure should not be limited by any particular embodiments described below.

Figure 2:
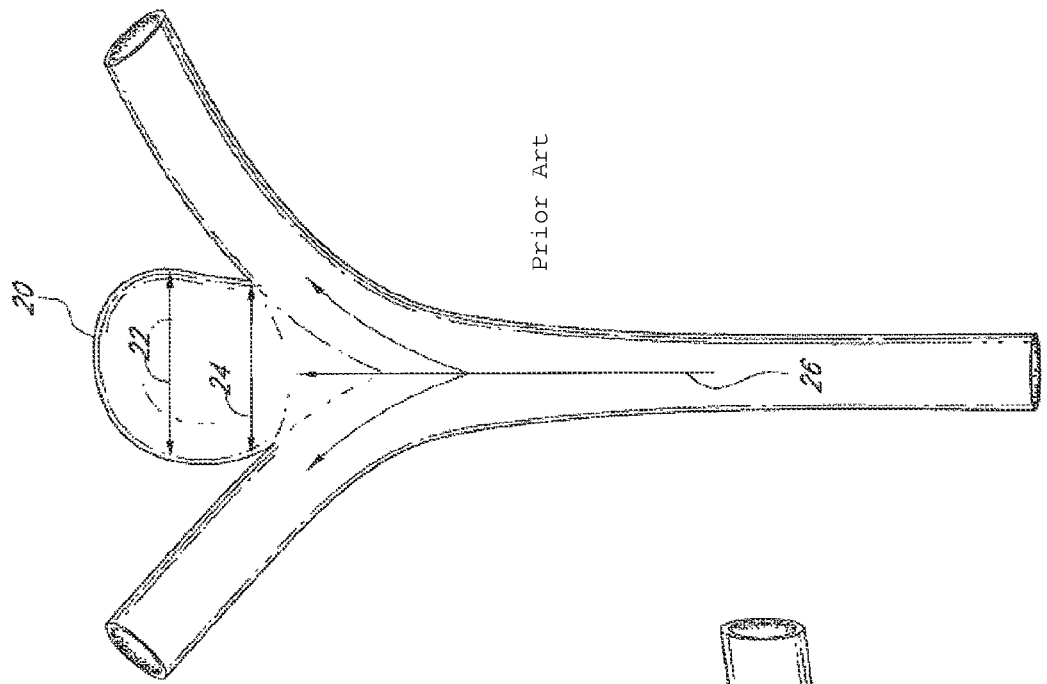
FIG. 2 illustrates an example embodiment of a bifurcation having an aneurysm.
Figure 1:
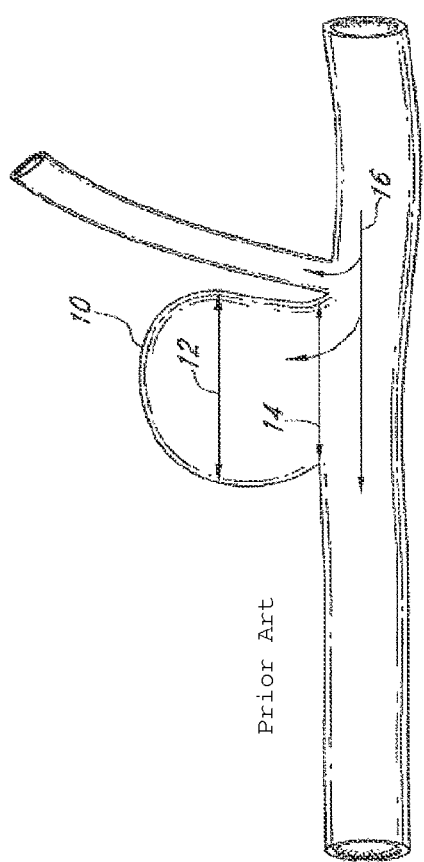
FIG. 1 illustrates an example embodiment of a side wall aneurysm.
Figure 4C:
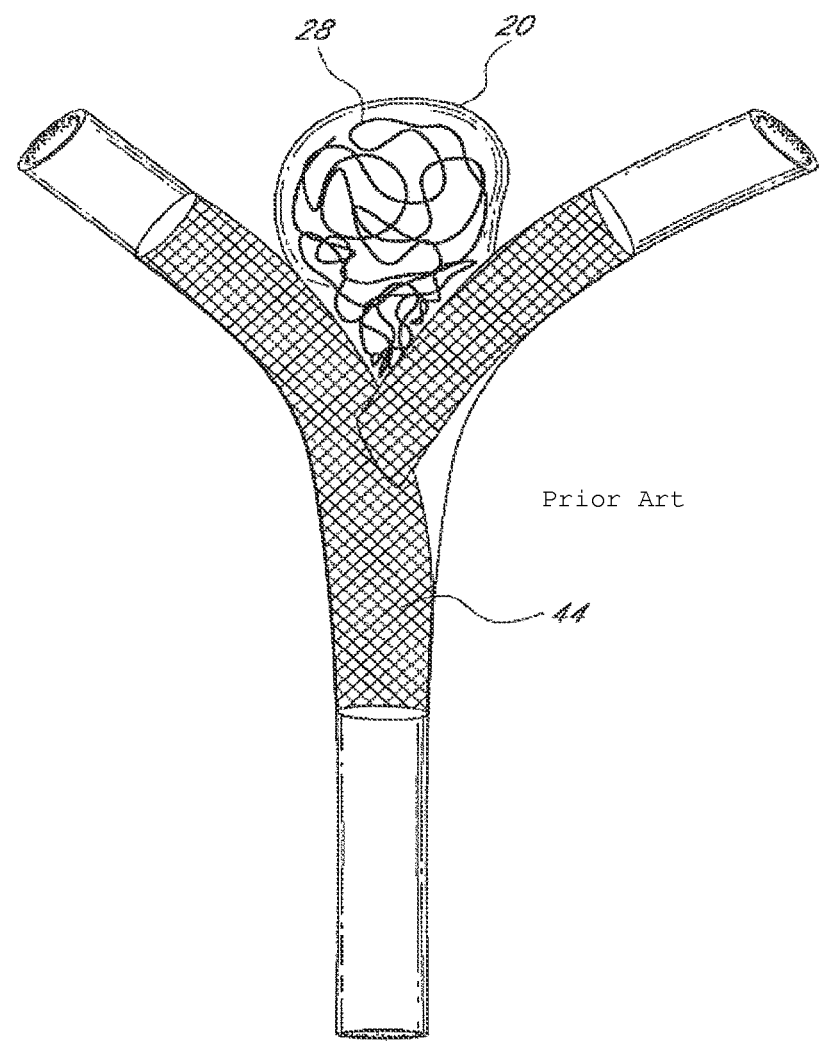
Figure 5:
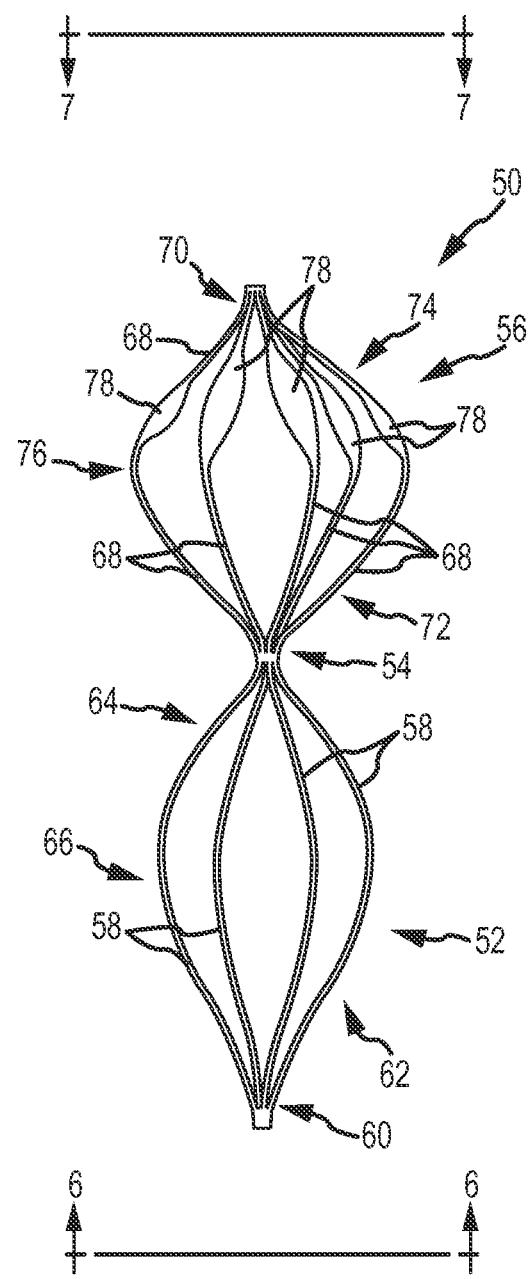
FIG. 5 illustrates an example embodiment of a vascular remodeling device.
Figure 6:
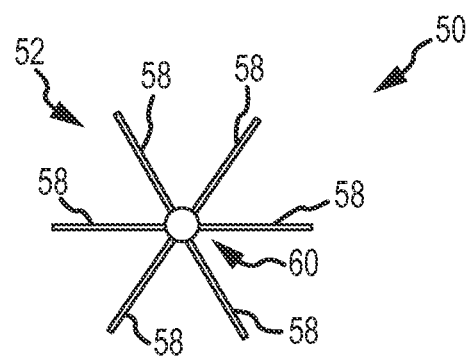
FIG. 6 illustrates a partial end view of the device of FIG. 5, taken along the direction indicated by the arrows 6-6 in FIG. 5.
Figure 7:
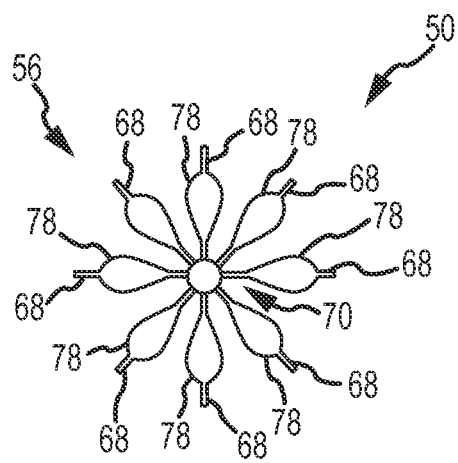
FIG. 7 illustrates a partial end view of the device of FIG. 5, taken along the direction indicated by the arrows 7-7 in FIG. 5.

FIGS. 5-7 illustrate an example embodiment of a vascular remodeling device 50. It will be appreciated that the device 50 may be more compliant than the vasculature in which it is deployed such that it may be somewhat misshapen after being deployed, and that certain shapes described herein are when the device 50 is an expanded (e.g., further expanded) state with no restriction. The device 50 comprises a proximal section 52 (or "bottom section" or "proximal portion" or "anchor portion"), an intermediate section 54 (or "middle section" or "junction" or "pivot junction"), and a distal section 56 (or "top section" or "distal portion"). The device 50 can be delivered via a catheter (e.g., microcatheter) into a bifurcation to support an aneurysm filling device with minimal interruption of blood flow in afferent and efferent vessels. In some embodiments, the device 50 may be retrieved and/or repositioned.

The proximal section 52 can be radially self-expanding and comprise a plurality of radially self-expanding struts 58. Six struts 58 are depicted in the proximal section 52 of FIGS. 5-6 (and only four of the struts 58 are visible in FIG. 5), but more or fewer struts may be employed in the proximal section 52, as described in further detail herein. The struts 58 converge toward the radial center of the proximal section 52 at the distal end of the proximal section 52, where the proximal section joins the proximal end of the intermediate section 54, and at the proximal end of the proximal section 52, where the proximal section joins a proximal end portion 60 of the device 50.

The proximal end portion 60, located at the proximal end of the device 50, may comprise a simple interconnection of the proximal ends of the struts 58, or it may comprise a coupling to facilitate delivery and/or re-sheathability and re-positionability of the device 50. Such a coupling may comprise an electrolytic, mechanical, chemical and/or instant detachment mechanism, configured to connect the device 50 to a delivery member such as a pusher wire.

When the device 50 is in the expanded configuration shown in FIGS. 5-7, the proximal struts 58 extend radially outward as they advance from the proximal and distal ends of the proximal section 52, thereby forming proximal and distal tapering portions or faces 62, 64 of the proximal section 52.

The struts 58 reach their radially outermost extent in a waist portion 66 of the proximal section 52, between the proximal and distal faces 62, 64. When the device 50 is deployed in a patient's vasculature, the waist 66 may engage a vessel wall to hold the proximal section 52 and device 50 in place as desired. (Depending on the shape or orientation of the vessel, bifurcation, etc., other portions of the proximal section 52 may engage the vessel wall in addition to or instead of the waist 66.) In the depicted waist portion 66, the struts 58 are curved and form curving radial crests or peaks. Alternatively, in the waist 66 the struts 58 can be flat and generally straight and parallel, to form an elongate and/or cylindrical waist 66.

The struts 58 of the proximal section 52 can have a substantially rectangular or flat cross section (e.g., where the struts 58 comprise uncut portions of a metallic tube or sheet). The struts 58 can alternatively have a substantially round (e.g., circular, elliptical, ovoid) cross section (e.g., where the struts 58 comprise round filaments). The proximal section 52 can comprise two or more struts 58, or between two and twelve struts 58. Although the proximal section 52 depicted in FIGS. 5-7 comprises six struts 58, the proximal section can alternatively comprise two, three, four, five, seven, eight, nine, ten, eleven or twelve struts 58. Still other numbers of struts are possible. As seen in FIG. 6, the proximal struts 58 may be equally angularly spaced and/or oriented around the central longitudinal axis of the device 50 (e.g., six struts 60° apart from each adjacent strut as shown in FIG. 6, two struts 180° apart from each other, three struts 120° apart, four struts 90° apart, etc.). Although the arrangement of the struts are shown in the figures as substantially isometric, the arrangement can place the struts in various angles relative to each other (e.g., six struts varying about 20°, about 40°, about 50°, about 70°, and about 80° apart from each adjacent strut). When the device 50 is placed at a bifurcation, the proximal section allows flow to efferent vessels because the struts 58 do not block fluid flow.

The tapered proximal face 62 of the proximal section 52 may allow the device 50 or portions thereof (e.g., the proximal section 52) to be retrieved back (e.g., in the proximal direction) into a delivery catheter via a distal opening thereof. For example, if the device 50 is being pulled into a catheter, the tapered proximal face 62 may radially compress the proximal section 52. The ability to retrieve the device 50 or proximal section 52 facilitates removal or re-positioning of the device 50 if an initial placement is not satisfactory.

The distal section 56 can be radially self-expanding and comprise a plurality of radially self-expanding struts 68. Eight struts 68 are depicted in the distal section 56 of FIGS. 5 and 7 (and only five of the struts 68 are visible in FIG. 5), but more or fewer struts may be employed in the distal section 56, as will be described in further detail below. The struts 68 converge toward the radial center of the distal section 56 at the proximal end of the distal section 56, where the distal section joins the distal end of the intermediate section 54, and at the distal end of the distal section 56, where the distal section joins a distal end portion 70 of the device 50.

When the device 50 is in the expanded configuration shown in FIGS. 5-7, the distal struts 68 extend radially outward as they advance from the proximal and distal ends of the distal section 56, thereby forming proximal and distal tapering portions or faces 72, 74 of the distal section 56. The struts 68 reach their radially outermost extent in a waist portion 76 of the distal section 56, between the proximal and distal faces 72, 74. When the device 50 is deployed in a patient's vasculature, the waist 76 may engage a vessel wall to hold the distal section 56 and device 50 in place as desired. (Depending on the shape or orientation of the vessel, bifurcation, etc., other portions of the distal section 56 may engage the vessel wall in addition to or instead of the waist 76.) In the depicted waist portion 76, the struts 68 are curved and form curving radial crests or peaks. Alternatively, in the waist 76 the struts 68 can be flat and generally straight and parallel, to form an elongate and/or cylindrical waist 76.

One or more of the struts 68 of the distal section 56 can optionally include or form widened portions or leaves 78 on the distal face 74 of the distal section. As best seen in FIG. 7, the widened portions 78 can provide a blocking function to prevent or reduce the passage of materials or fluids through the distal face 74. For example, in one aspect, the widened portions may be wider than a width of the struts forming the proximal face of the distal section.

In another aspect, the widened portions may comprise a first and second ramp, where the first ramp extends from an edge of the strut to an edge of the widened portion, and the second ramp extends from the edge of the widened portion to the edge of the strut. In this manner, the widened portions 78 can help support aneurysm filling materials or devices (such as coils or embolic materials) within an aneurysm, and/or reduce or block fluid flow through the distal face 74 to promote thrombogenicity and increase the occlusiveness of the distal face.

Instead of or in addition to the widened portion(s) 78, a mesh, membrane or other covering may be employed on the distal face 74 to perform similar function(s). Notwithstanding the presence of the widened portion(s) 78, mesh, membrane or other covering, the distal face 74 can include sufficient open space to allow a microcatheter or other similar device to pass through, to place coils or other aneurysm filling materials or devices in an aneurysm covered by the distal face 74.

The distal section 56 can therefore allow for safe and controlled placement of coils, and can be designed to support a certain packing density of coil. If desired, the widened portion(s) 78, mesh, membrane or other covering can block fluid and material passage through the distal face 74 of the distal section 56 to a degree sufficient to provide a flow diversion effect, and serve as a flow diverter, which may allow omission of any coils or other aneurysm filling materials or devices.

The struts 68 of the distal section 56 can have a substantially rectangular or flat cross section (e.g., where the struts 68 comprise uncut portions of a metallic tube or sheet). The struts 68 can alternatively have a substantially round (e.g., circular, elliptical, ovoid) cross section (e.g., where the struts 68 comprise round filaments). A circular, elliptical or ovoid cross-section may be imparted to otherwise square or rectangular struts 58/68 by processing steps such as electropolishing. The distal section can comprise two or more struts 68, or between two and twelve struts 68. Although the distal section 56 depicted in FIGS. 5-7 comprises eight struts 68, the distal section can alternatively comprise two, three, four, five, six, seven, nine, ten, eleven or twelve struts 68. Still other numbers of struts are possible. As seen in FIG. 7, the distal struts 68 may be equally angularly spaced and/or oriented around the central longitudinal axis of the device 50 (e.g., eight struts 45° apart from each adjacent strut as shown in FIG. 6, two struts 180° apart from each other, three struts 120° apart, four struts 90° apart, etc.). When the device 50 is placed at a bifurcation, the proximal face 72 of the distal section 56 allows flow to efferent vessels because the struts 68 of the proximal face 72 do not block fluid flow.

The tapered proximal face 72 of the distal section 56 may allow the device 50 or portions thereof (e.g., the distal section 56) to be retrieved back (e.g., in the proximal direction) into a delivery catheter via a distal opening thereof. For example, if the device 50 is being pulled into a catheter, the tapered proximal face 72 may radially compress the distal section 56. The ability to retrieve the device 50 or distal section 56 facilitates removal or re-positioning of the device 50 if an initial placement is not satisfactory.

One or both of the proximal and distal sections 52, 56 can optionally be generally spherical in shape when in the expanded or deployed state.

The intermediate section 54 connects the proximal section 52 and the distal section 56, and can be relatively short and relatively narrow (relative to the length and width of the proximal and distal sections 52, 56 when they are expanded). The intermediate section 54 can be located in a radially central region of the device 50, and can be confined to that radially central region (e.g., the device 50 can lack any interconnection between the proximal and distal sections 52, 56 radially outward of the intermediate section 54). So configured, the intermediate section 54 allows the distal section 56 to pivot with respect to the proximal section and thereby allow the device 50 to be deployed in tortuous vasculature.

Figure 8:
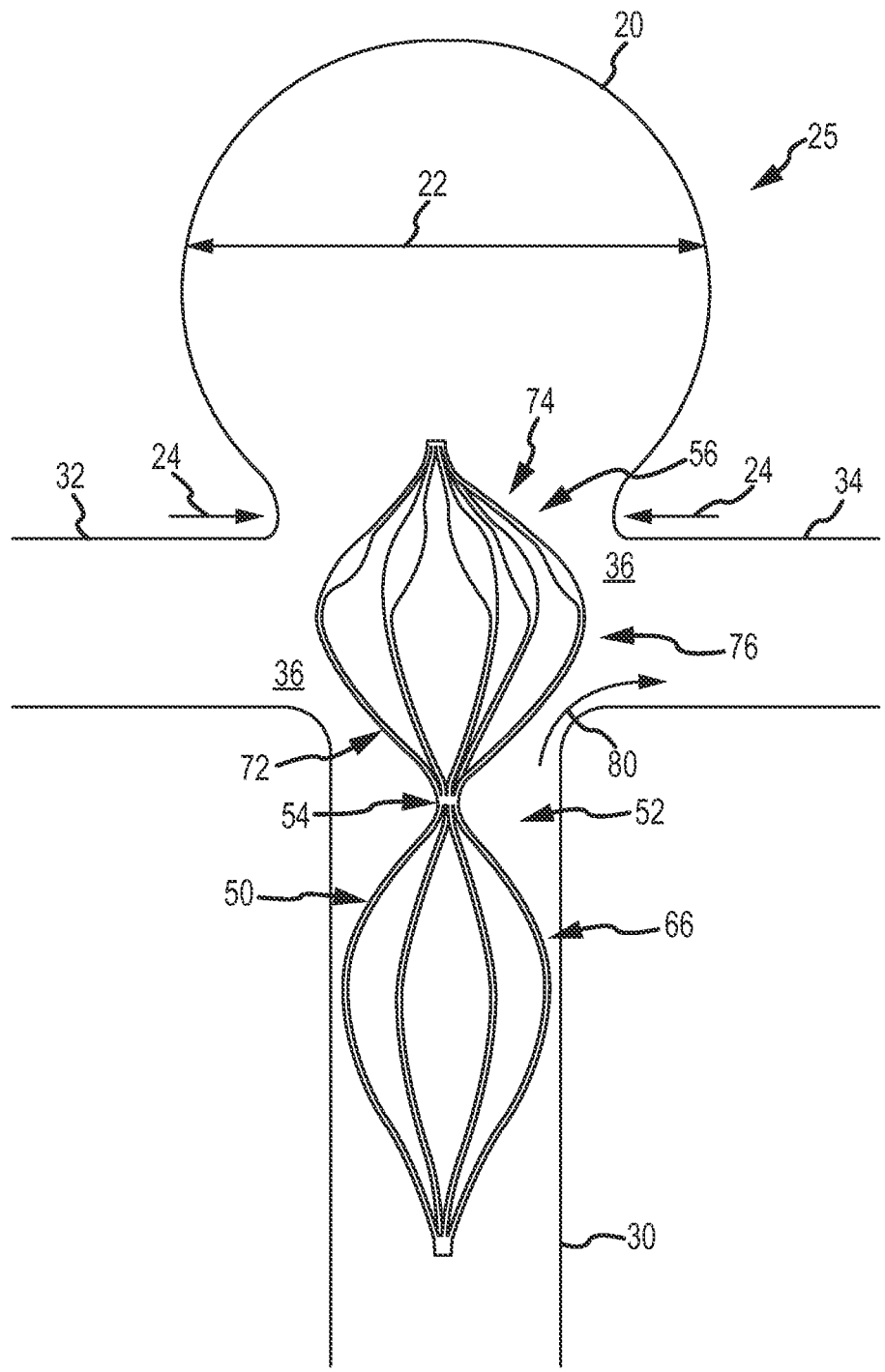
FIG. 8 illustrates the device of FIG. 5 in an example of a use environment in a vascular bifurcation with an aneurysm.
Figure 9:
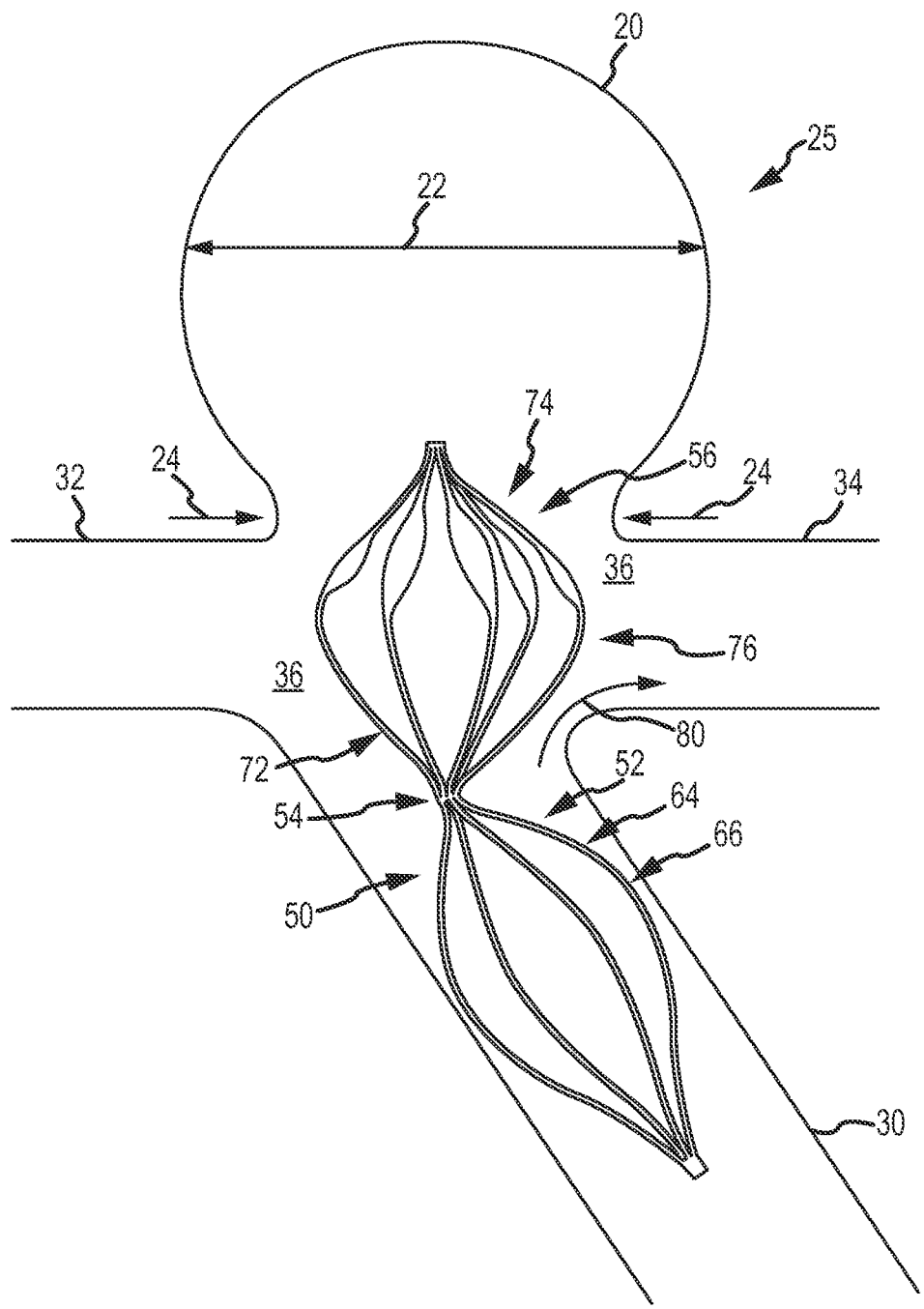
FIG. 9 illustrates the device of FIG. 5 in an example of a use environment in a vascular bifurcation with an aneurysm and an angled or curving parent vessel.

The intermediate section 54 may permit "multiaxial" pivoting or tilting, e.g. at least about a first axis through the intermediate section 54 and orthogonal to the plane of the page in FIGS. 5 and 8-9, and about a second axis through the intermediate section 54 and orthogonal to the first axis. The intermediate section 54 may permit "omniaxial" pivoting or tilting, about the first and second axes described above, and any radially-oriented axis passing through the intermediate section 54.

The intermediate section 54 may comprise a relatively short uncut tube defining a generally tubular outer surface and the proximal and distal struts 58, 68 can comprise proximal and distal extensions of the intermediate section 54 and its tubular outer surface, and be integral and monolithic with the intermediate section 54 and its outer surface. The struts 58, 68 can extend radially outward as they extend proximally (proximal struts 58) and distally (proximal struts 68) from the proximal and distal ends, respectively, of the intermediate portion 54. The proximal struts 58 and/or the distal struts 68 can be co-cylindrical with the intermediate portion 54 where they join the intermediate portion 54 at its proximal and distal ends, respectively. Where they join the intermediate portion 54, the proximal struts 58 and/or the distal struts 68 can be wider (in the circumferential direction with respect to the tubular form of the intermediate portion) than they are thick, and of similar thickness as the sidewall of the intermediate portion 54.

The device 50 may provide multiaxial or omniaxial pivoting or tilting up to relatively high deflection angles (e.g., up to 90 degrees) without significantly affecting the ability of the proximal and distal sections 52, 56 to maintain their expanded states and engage the adjacent portions of the bifurcation 25 (see FIGS. 8, 9). This capability can be facilitated by making the proximal struts 58 independent of the distal struts 68, e.g. as depicted in FIGS. 5, 8-11, 13 and 16. The two groups of struts are independent of each other in that forces acting solely on, and/or deflections occurring solely in, the proximal struts 58 do not significantly affect the ability of the distal struts 68 to maintain their expanded state and/or maintain engagement with adjacent portions of the bifurcation 25, and forces acting solely on, and/or deflections occurring solely in, the distal struts 68 do not significantly affect the ability of the proximal struts 58 to maintain their expanded state and/or maintain engagement with adjacent portions of the bifurcation 25.

One, some or all of the struts 58 can bend or pivot with respect to the intermediate section 54 independently of one, some or all of the struts 68, and vice versa. The intermediate section 54 may promote independence by interconnecting the struts 58 and the struts 68 in a radially central region of the device 50, and physically and functionally separating them, absorbing bending stresses from the struts 58 and the struts 68 rather than transmitting them from the struts 58 to the struts 68 or vice versa.

Instead of or in addition to independence of the proximal struts 58 as a group, from the distal struts 68 as a group, the struts 58 may be independent of each other (within the group of struts 58), and/or the struts 68 may be independent of each other (within the group of struts 68). In the device 50 as depicted in FIGS. 5-9, the proximal struts 58 are independent of each other and the distal struts 68 are independent of each other. Each proximal strut 58 can bend or pivot with respect to the intermediate section 54 independently of the other proximal struts 58, and each distal strut 68 can bend or pivot with respect to the intermediate section 54 independently of the other distal struts 68. Independence is promoted within each group of struts 58, 68 by interconnecting them only at their proximal and distal ends, and in a radially central region of the device 50.

It should be noted, however, that independence as used herein does not exclude interconnecting independent components by members (e.g. membranes, very fine wires and the like) that are insufficiently rigid to cause one component to significantly affect the action of the other. The proximal struts 58 and/or the distal struts 68 can also be independent of each other, but only within a limited region of the proximal section 52 and/or distal section 58. For example, the proximal struts 58 may be independent of each other within the distal face 64 of the proximal section, and/or the distal struts 68 may be independent of each other within the proximal face 72 of the distal section 56.

The tapered distal face 64 of the proximal section 52 and tapered proximal face 72 of the distal section 56 also allow the sections 52, 56 to pivot significantly without contact between the sections 52, 56 other than at the intermediate section 54.

The intermediate section 54 can be rigid or flexible. Where the intermediate section 54 is rigid, the pivotability of the device 50 can be provided by the flexibility and/or independence of the struts 58 in the distal face 64 of the proximal section 52 and of the struts 68 in the proximal face 72 of the distal section 56. In this example, the proximal and distal sections are able to pivot multiaxially relative to each other without requiring plastic deformation of the intermediate section. Each of struts 58 and struts 68 may be capable of flexing, extending, bowing, straightening, bending, or other elastic or plastic deformation along the length or a portion thereof.

As struts 58 and struts 68 independently flex and extend, sections 52, 56 can pivot about intermediate section 54 and relative to each other. For example, struts on one side of a section may flex (e.g., bend), and struts on an opposing side of a section may extend (e.g., straighten), whereby the section pivots about the region where the struts connect to intermediate section 54.

According to embodiments, such action is facilitated along one or more sections of the device. According to embodiments, this pivot action is provided without requiring plastic deformation of intermediate section 54 or any action along the length of intermediate section 54. The intermediate section 54 can comprise a short length of hypotube (e.g., a short length of uncut hypotube when the proximal and/or distal sections 52, 56 are cut from the hypotube) which may be flexible or rigid. According to embodiments, the intermediate section 54 can comprise a flexible coil, longitudinally oriented such that its winds spiral around the central longitudinal axis of the device 50, or the intermediate section 54 can comprise a ball-and-socket joint, a length of flexible wire, or other flexible member.

The device 50 can further comprise one or more radiopaque markers (e.g. coils) coupled to or wound around portions of the device. For example, the device 50 can include radiopaque markers on one, two or all three of the proximal end portion 60, intermediate section 54, and distal end portion 70. Instead of or in addition to those markers, the device 50 can include radiopaque markers on one or more of the struts 58, and/or on one or more of the struts 68. According to embodiments, when any of the proximal end portion 60, intermediate section 54, or distal end portion 70 defines a central lumen therethrough (e.g., when the device 50 is cut or etched from a tube or sheet), radiopaque material may be placed within some, one or all of those lumens to make the portion(s) 60/54/70 radiopaque. For example, radiopaque material maybe provided within a lumen of at least one of portion(s) 60/54/70 with securement at one or both of the ends of the lumen.

The device 50 can comprise a self-expanding, super elastic, and/or a shape-memory material (e.g., comprising Nitinol, CoCr alloy, shape memory polymers (e.g., polyglycolic acid, polylactic acid), etc.), thereby causing the device 50 to be self-expanding under certain conditions (e.g., when not restrained by a catheter). In some embodiments, the proximal section 52, the intermediate section 54, and/or the distal section 56 may comprise different materials. For example, the distal section 56 may comprise polymer material while the proximal section 52 and the intermediate section 54 comprise metallic material, a different polymer material, etc. For another example, the distal section 56 may comprise metallic material while the proximal section 52 and the intermediate section 54 comprise different metallic materials, polymer material, etc. Other combinations of materials are also possible. The device 50 can assume a low profile compressed state (e.g., confined within a catheter) for delivery. When cut from a tube or sheet, the device 50 may assume substantially the diameter of the tube or rolled sheet when in the compressed state. Upon deployment from the catheter, the device 50 expands from the compressed state to an expanded state.

FIG. 8 depicts one example of the device 50 in use, positioned at a junction 36 of a bifurcation 25 (e.g., a neurovascular bifurcation (e.g., the basilar tip area)) comprising at least one afferent or parent vessel 30, efferent or branch vessels 32, 34, the junction 36 of the vessels 30, 32, 34, and an aneurysm 20 having a fundus 22 and a neck 24. The proximal section 52 is positioned in the parent vessel 30 in an expanded state, such that the waist 66 contacts the inner wall of the vessel 30. Where the proximal section 52 is self-expanding, the struts 58 are biased radially outward and the struts in the waist 66 may engage or "grip" the vessel wall, thereby anchoring the proximal section 52 and the device 50 in the parent vessel 30. The distal section 56 is positioned in the junction 36 in an expanded state, such that the waist 76 contacts the inner wall of the junction 36. Where the distal section 56 is self-expanding, the struts 68 are biased radially outward and the struts in the waist 76 may engage or "grip" the junction wall, thereby anchoring the distal section 56 and the device 50 in the junction 36. The struts 68 of the distal section 56 may also center the distal section 56 (and the distal face 74 thereof) in the junction 36 and/or aneurysm neck 24.

When the proximal and distal sections 52, 56 are in their expanded state, the friction force developed between the proximal section 52 and the inner wall of the parent vessel 30, and/or the friction force developed between the distal section 56 and the inner wall of the junction 36, may suffice to prevent the device 50 from moving significantly in the proximal direction, away from the aneurysm 20 and in the distal direction, toward the aneurysm 20.

In the implementation depicted in FIG. 8, the distal face 74 of the distal section 56 extends into and occupies at least a portion of the neck 24 of the aneurysm 20. The struts 68 and widened portion(s) 78 (or another structure, such as a mesh or membrane) make the distal face 74 sufficiently low in porosity that the face 74 and device 50 can act as a scaffolding to inhibit or prevent herniation or prolapse of objects (e.g., embolization coils or materials, thrombi, etc.) out of the neck 24 of the aneurysm 20.

The device 50 can permit blood to flow from the parent vessel 30 to the efferent vessels 32, 34 of the bifurcation. The proximal section 52 presents minimal axially-facing or proximally-facing surface area (see FIG. 6) toward oncoming blood flow in the parent vessel 30 so that blood passes through the proximal section 52 with little or no blockage. The proximal face 72 of the distal section 56 likewise presents minimal axially-facing or proximally-facing surface area toward blood flow that has passed through the proximal section 52, so that such blood passes into or through the distal section 56 with little or no blockage. In addition, depending on the manner in which the device 50 is positioned in the bifurcation 25, blood that has passed through the proximal section 52 may flow around the distal section 56 and into one or both efferent vessels 32, 34 (indicated by arrow 80 in FIG. 8), instead of or in addition to blood that flows through the distal section 56 and into the vessel(s) 32, 34.

The depicted distal face 74 of the distal section 56 is configured to impede or block blood flow therethrough, via the widened portions 78 and/or other structures as disclosed elsewhere herein. Accordingly, blood tends to stagnate in and around the distal face 74, promoting thrombogenesis, occlusion of the aneurysm 20, and retention of any filling materials and thrombi in the aneurysm.

FIG. 9 depicts another example of the device 50 in use, positioned at a junction of a bifurcation 25 which is similar to that depicted in FIG. 8, with the exception that the parent vessel 30 is significantly angled or curved with respect to the efferent vessels 32, 34, the junction 36, and/or the aneurysm 22. For example, in such a bifurcation the central axis of the parent vessel 30 can be non-coaxial and non-parallel with a central axis of the junction 36 and/or a central axis of the aneurysm 20.

As depicted in FIG. 9, the various components of the device 50 perform the same functions in the same manner as described with regard to FIG. 8, except that the proximal and distal portions 52, 56 are not coaxial, but are in a tilted orientation (e.g., their respective central axes form an included angle of less than 180 degrees). In addition, one, two or all three of (a) the intermediate portion 54, (b) the struts 58 of the distal face 64 of the proximal portion 52, and (c) the struts 68 of the proximal face 72 of the distal portion 56, may flex or pivot to accommodate the tilted orientation of the portions 52, 56 with respect to each other. In this manner, despite the tortuosity of the bifurcation 25, the proximal portion 52 can engage the parent vessel 30 and support the distal portion 56 in the junction 36 and neck 24 sufficiently to prevent significant migration of the device 50 in the distal or proximal directions, and the distal portion 56 can be approximately centered within the junction 36 and neck 24 (and, where appropriately configured, can engage the inner wall of the junction 36 to provide additional anti-migratory support).

To facilitate tilting/flexing/pivoting in the manner depicted in FIG. 9, the connections of the struts 58 and/or the struts 68 to the intermediate portion 54 may be configured to provide pivoting action, such as by making the struts 58/68 slightly thinner where they meet or connect to the intermediate portion 54. Such a pivotable arrangement of the struts and intermediate portion may allow the portions 52 and 56 to tilt with respect to each other without significantly buckling or deforming the struts and altering the expanded shape of the portions 52, 56. In other words, the pivoting connections of the struts 58/68 to the intermediate portion (instead of, or in addition to, a flexible intermediate portion 54) can relieve some or all of the bending stress imparted to the struts 58/68 when the device 50 takes on a tilted orientation as in FIG. 9. These structural features may be employed instead of or in addition to others disclosed herein to promote pivoting/tilting the sections 52, 56 without substantially affecting their ability to remain expanded or engage adjacent portions of the bifurcation. The device 50 may be configured to allow the portions 52, 56 to tilt/flex/pivot with respect to each other up to 90 degrees.

Figure 10:
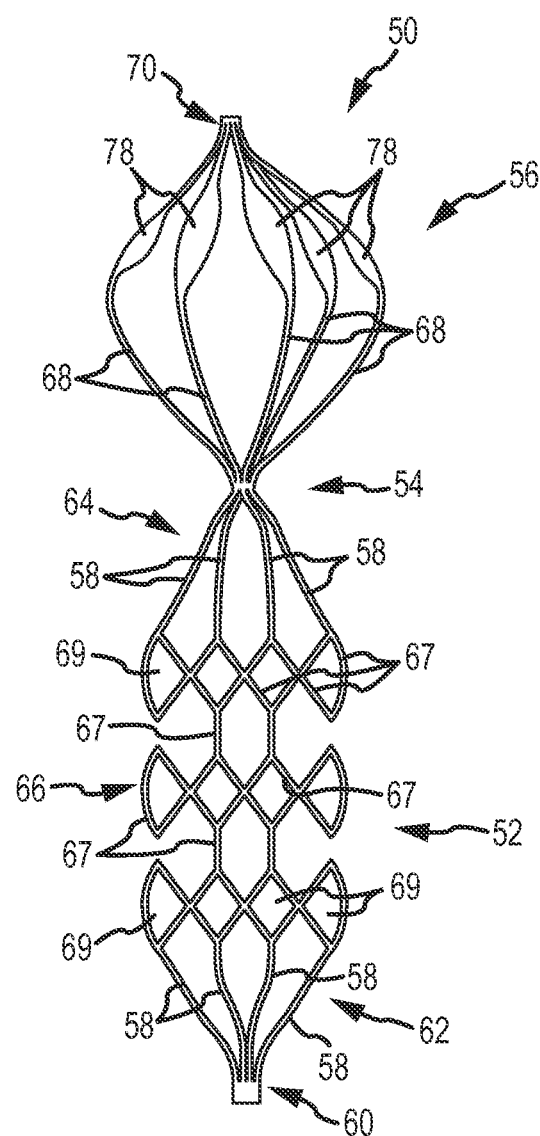
FIG. 10 illustrates a variation of the device of FIG. 5, in which a proximal section of the device forms an extended waist portion.
Figure 11:
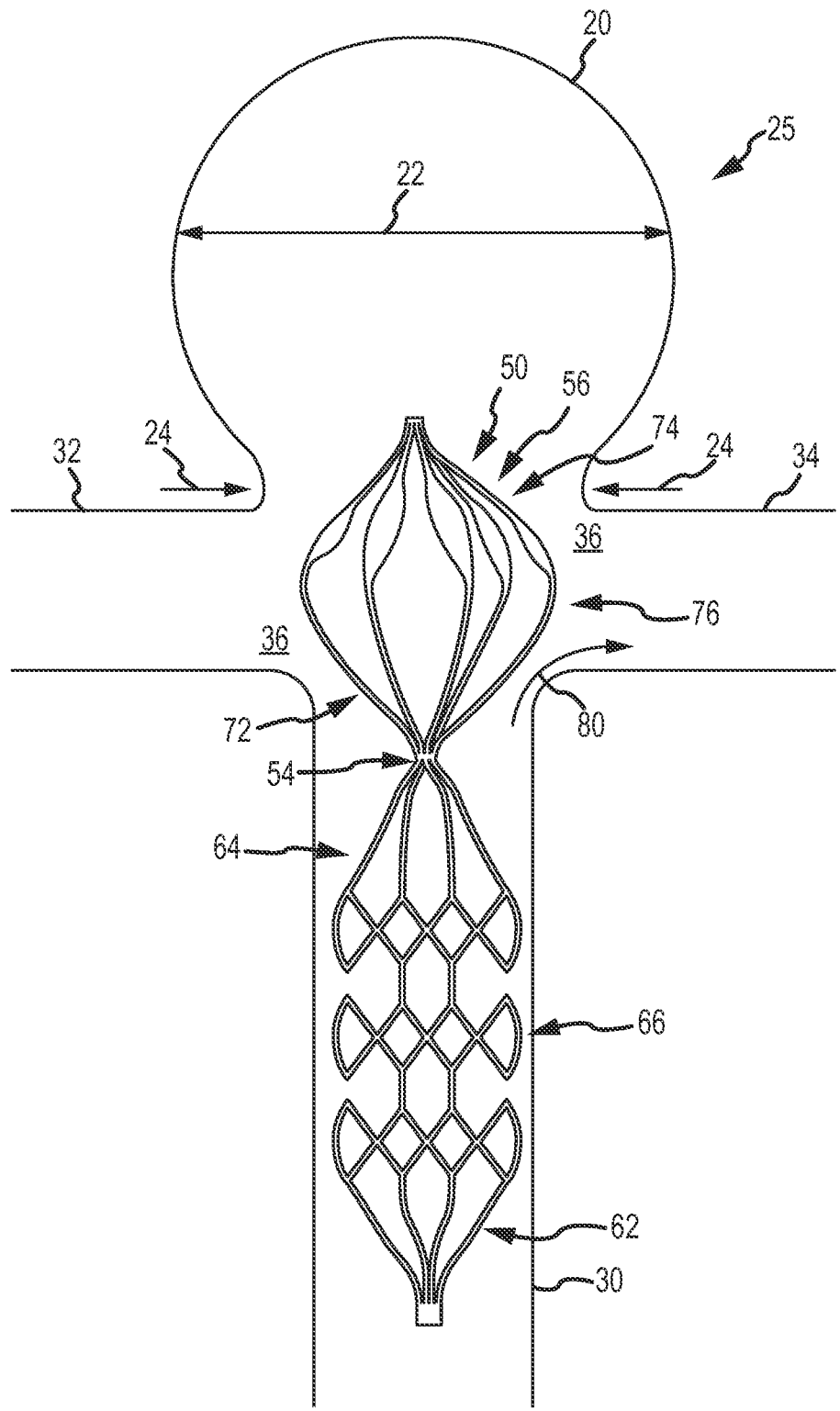
FIG. 11 illustrates the device of FIG. 10 in an example of a use environment in a vascular bifurcation with an aneurysm.

FIGS. 10-11 depict another example of the device 50, which can be similar in structure, function, methods of use and construction, etc. to the device 50 described herein with reference to FIGS. 5-9, except as further described herein. Accordingly, like reference numerals refer to like components in FIGS. 5-9, on the one hand, and FIGS. 10-11 on the other hand, except where a description or depiction to the contrary is provided expressly herein. In the device 50 of FIGS. 10-11, the waist 66 comprises a number of waist members 67 that interconnect both laterally (e.g., circumferentially) and longitudinally. The waist members 67 can thus form a number of bands of diamond forms 69 which are expandable in circumference to engage or grip the inner wall of the parent vessel 30 when the device 50 is in use. The waist members 67 can be arranged in circumferentially expandable patterns other than the one depicted in FIGS. 10-11, with or without the use of diamond forms 69.

The struts 58, and the proximal and distal faces 62, 64 of the proximal section 52, can be similar to those described herein with reference to the device 50 of FIGS. 5-9. In the device 50 of FIGS. 10-11 the proximal face 62 of the proximal section 52 and the proximal end portion 60 may be omitted altogether, to create a device 50 with an open proximal end.

In a variation of the device 50 of FIGS. 5-9, or of the device 50 of FIGS. 10-11, the waist 66 can comprise an expandable woven mesh, woven from filaments of any material disclosed herein as suitable for constructing the device 50. Such a woven mesh can be cylindrical in form, with the distal edge thereof connected to the proximal ends of the struts 58 of the distal face 64 of the proximal portion 52. The proximal edge of the cylindrical mesh can be connected to the distal ends of the struts 58 of the proximal face 62 of the proximal portion 52. According to embodiments, the proximal face 62 of the proximal section 52 and the proximal end portion 60 may be omitted altogether, to create a device 50 with an open proximal end.

FIG. 11 depicts one example of the device 50 of FIGS. 10-11 in use, positioned at a junction 36 of a bifurcation 25 in a manner similar to that depicted in FIG. 8. The proximal section 52 is positioned in the parent vessel 30 in an expanded state, such that the waist 66 contacts the inner wall of the vessel 30. Where the proximal section 52 is self-expanding, the struts 58 are biased radially outward and the waist member 67 and diamond forms 69 are biased to a circumferentially expanded state so that the waist 66 engages or "grips" the vessel wall, thereby anchoring the proximal section 52 and the device 50 in the parent vessel 30. Furthermore, the functions, modes of action, and methods of use of these and the other components of the device 50 of FIGS. 10-11 are the same as described elsewhere herein (including in connection with FIGS. 8-9) for the device 50 of FIGS. 5-9.

Figure 12:
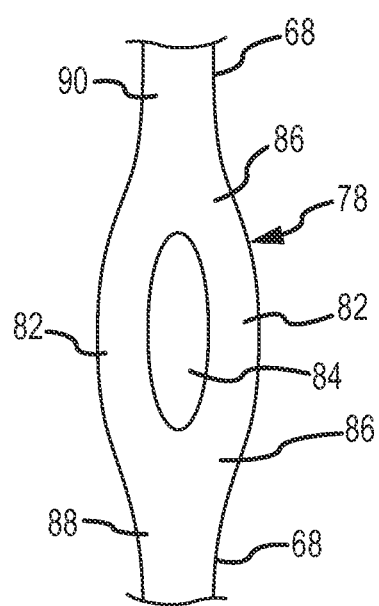
FIG. 12 illustrates an example configuration of a widened portion for use on struts of the device of FIG. 5 or the device of FIG. 10.

FIG. 12 depicts one example of a widened portion 78 that may be employed with any of the embodiments of the device 50 disclosed herein. One, some or all of the widened portions 78 (and struts 68) of the device 50 may take the form depicted in FIG. 12 and further described herein. To form the widened portion 78, the strut 68 can be longitudinally split into sub-struts 82 that surround an opening 84 in the widened portion 78. The opening 84 can be left as an open space, in which case the thrombogenicity of the distal face 74 of the distal section 56 is enhanced by the division of the struts 68 of the distal face into a larger number of narrower, spread-apart sub-struts 82. According to embodiments, the opening 84 can be filled or covered with radiopaque material, and/or radiopaque coils can be wound around the sub-struts 82. According to embodiments, a combination of open and covered/filled radiopaque widened portions 78, and sub-struts 82 bearing radiopaque coils, can be employed. The widened portions may also alternate or vary in size from one strut 68 to the next.

The struts 68 can be configured to form the sub-struts 82 and opening 84 via tapering portions 86 on either side of the opening 84. Distal and proximal of the tapering portions 86, the struts 68 can be of substantially uniform width. The proximal portion 88 of the strut 68 (proximal of the widened portion 78) can be wider than the distal portion 90 of the strut 68 (distal of the widened portion 78). In such a case, the width of the proximal strut portion 88 can nonetheless be substantially uniform from the proximal tapering portion 86 to the intermediate portion 54, and the width of the distal strut portion 90 can be substantially uniform (but narrower than the width of the proximal strut portion 88) from the distal tapering portion 86 to the distal tip portion 70 of the device 50. By employing struts 68 that are narrower in their distal portions 90 than in their proximal portions 88, the distal face of the distal portion 56 can be made relatively compliant and therefore more easily conformable to any embolic material in the aneurysm 20, while retaining a desired degree of stiffness in the proximal components of the device 50.

The various versions of the vascular remodeling device 50 disclosed herein (e.g. the devices 50 of FIGS. 5-12) can be manufactured in a process comprising cutting (or electrochemically etching) and shaping a metallic tube or sheet (e.g., a laser cut hypotube or sheet). A laser or electrochemical etcher may cut out portions of the tube, leaving in place the various structural elements of the proximal section 52, the intermediate section 54, and/or the distal section 56. In the device 50 depicted in FIGS. 5-9 and 12, or the device 50 depicted in FIGS. 10-12, the proximal section 52, the intermediate section 54, and the distal section 56 can be integrally formed from a metallic tube and not cut away from each other. In devices 50 in which all sections 52, 54, 56 are integrally fabricated by being cut, etched, etc. from the same tube or sheet, the device 50 is of single-piece construction, taking the form of a single, partial tube or sheet. Alternatively, the sections 52, 54, 56 can be formed separately and then assembled together using any suitable technique, such as welding, gluing, interlocking, crimping, swaging, braiding, deposition, etc. Where the intermediate section 54 comprises a coil, the sections 52 and 56 may be formed from the same or separate tubes, and then attached to either end of the coil using any such suitable technique.

After cutting from one or more tubes, the device 50 or section(s) 52/54/56 thereof may be reshaped and heat treated to impart shape setting to the device or section(s). The shape setting process may include several steps comprising, for example, stretching and confining the cut tube into a new shape during the heat treatment. At the end of each heat treatment step, the cut tube assumes the shape in which it was confined during the heat treatment process. The final shape (e.g., expanded state) and size may obtained by several such steps. The device 50 or cut tube may be electropolished during manufacture, which can reduce the initial wall thickness of the tube to a final, desired thickness.

Although the device 50 is depicted in its expanded state in FIGS. 5-11, the device 50 can have a contracted state in which the proximal and distal sections 52, 56 take on a smaller diameter than in the expanded state. For example, in the contracted state the sections 52, 56 can have a diameter small enough to fit within a delivery device, such as a microcatheter. Where the sections 52, 54, 56 are cut from a single tube, the diameter of one or both of the proximal and distal sections 52, 56 when in the contracted state can be substantially equal to the diameter of the tube from which the device 50 is cut, and/or substantially equal to the diameter of the intermediate section 54.

The table below provides an example set of dimensions that can be employed in constructing the device 50 of FIGS. 5-9 and 12. Such a device 50 can have a proximal section 52 with six struts 58, and a distal section 56 with eight struts 68. The table below also provides an example set of dimensions for all components of the device 50 of FIGS. 10-12 that are common with the device 50 of FIGS. 5-9 and 12. The dimensions provided below should not be taken as limiting with respect to the device 50 of FIGS. 5-9 and 12 or the device 50 of FIGS. 10-12. One, several or all of these dimensions can be disregarded when constructing the device 50 of FIGS. 5-9 and 12 or the device 50 of FIGS. 10-12.

| Component | Dimension | Size |
| --- | --- | --- |
| proximal section 52 | diameter at waist 66 (expanded) | 3-14 mm |
|  | diameter at waist 66 (contracted) | 0.015 in., 0.010-0.030 in. |
|  | length (expanded) | 10 mm, 2-20 mm or more |
|  | width of struts 58 | 0.0045 in., 0.003-0.006 in. |
|  | thickness of struts 58 | 0.0015 in., 0.001-0.004 in. |
| intermediate section 54 | length | 0.15 mm, 0-5 mm |
|  | diameter | 0.015 in., 0.010-0.030 in. |
|  | wall thickness | 0.0015 in., 0.001-0.004 in. |
| distal section 56 | diameter at waist 76 (expanded) | 2-20 mm, 4-15 mm |
|  | diameter at waist 76 (contracted) | 0.015 in., 0.010-0.030 in. |
|  | length (expanded) | 2-20 mm, 4-15 mm |
|  | width of struts 68 | 0.0035 in. (proximal of widened portions 78) 0.003 in. (distal of widened portions 78) |
|  | thickness of struts 68 | 0.0015 in., 0.001-0.004 in. |
|  | width of sub-struts 82 | 0.002 in., 0.001-0.003 in. |
|  | thickness of sub-struts 82 | 0.0015 in., 0.001-0.004 in. |
|  | length of opening 84 | 2-5 mm |
|  | width of opening 84 | 0.5-4 mm |

Figure 13:
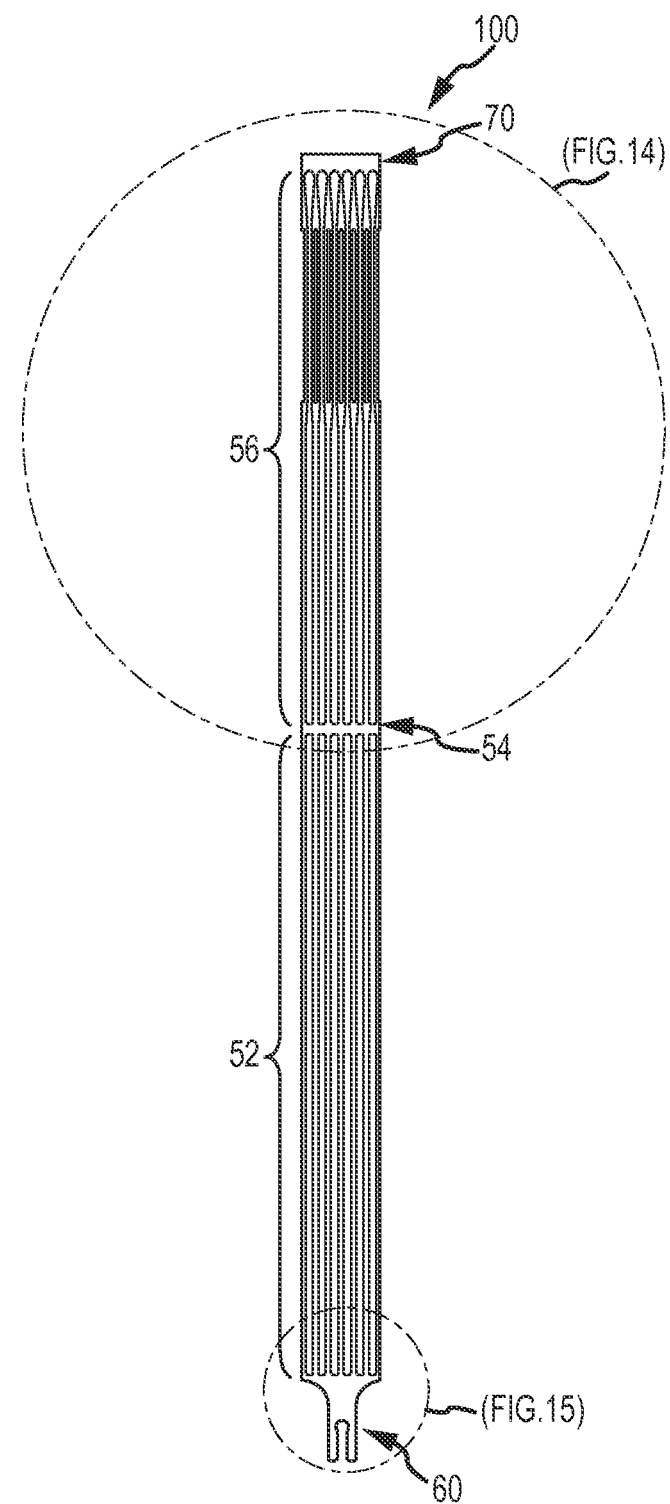
FIG. 13 illustrates a cut pattern for use in making a device similar to the device of FIG. 5, but with six struts in the distal section thereof.
Figure 14:
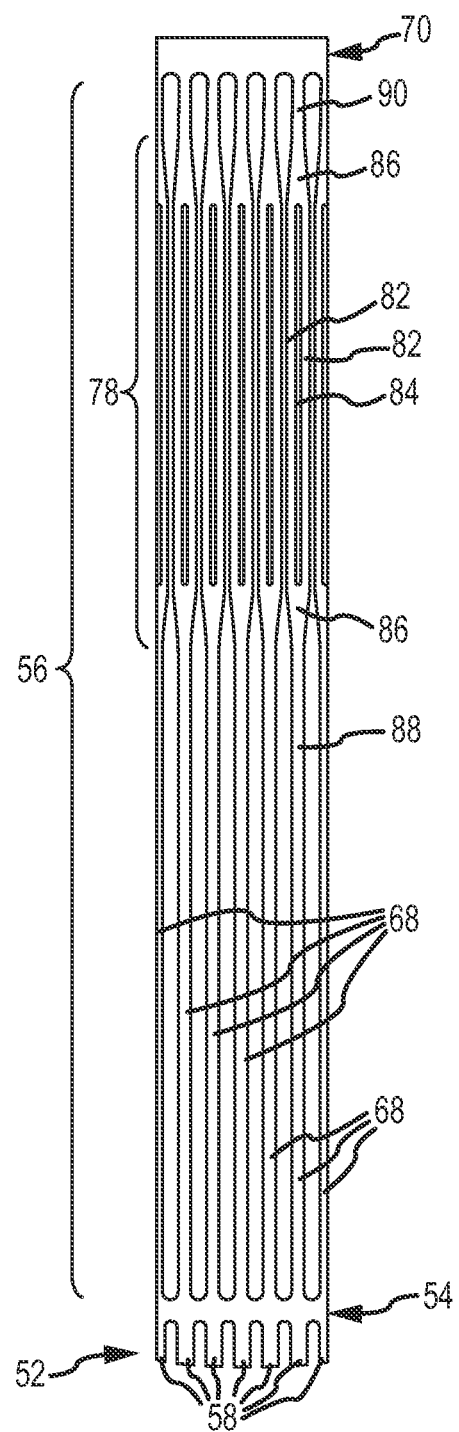
FIG. 14 is a detail view illustrating the distal section and part of the proximal section of the cut pattern of FIG. 13.
Figure 15:
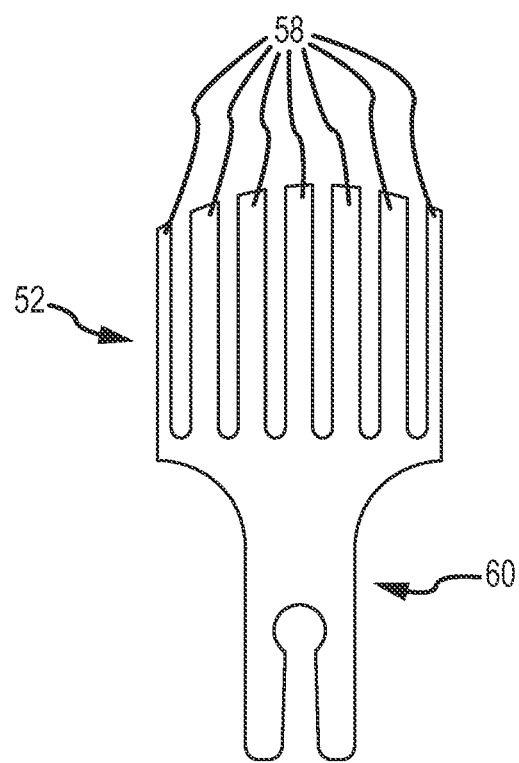
FIG. 15 is a detail view illustrating a proximal end portion of the cut pattern of FIG. 13.

FIGS. 13-15 depict an example of a cut pattern 100 that can be employed (e.g., in laser cutting or etching a hypotube or sheet) to construct the device 50 of FIGS. 5-9 and 12. The cut pattern 100 of FIGS. 13-15 is suitable for a device 50 having six struts 68 in the distal portion 56; otherwise, the device 50 formed via the cut pattern 100 can be similar in structure, function and method of use to the device 50 depicted in FIGS. 5-9 and 12 and described elsewhere herein. The cut pattern 100 provides uncut areas that form the various components of the device 50. Those components of the device 50 are marked in FIGS. 13-15 with the same reference numerals as in FIGS. 5-9 and 12 (and, for common components, as in FIGS. 10-11).

Figure 18:
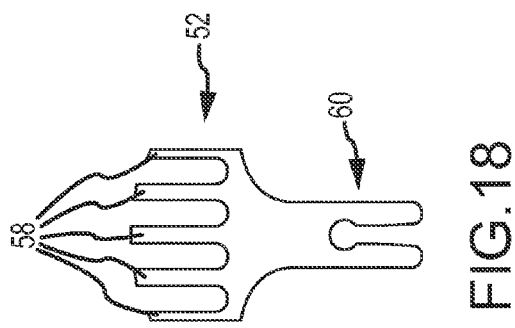
FIG. 18 is a detail view illustrating a proximal end portion of the cut pattern of FIG. 16.
Figure 17:
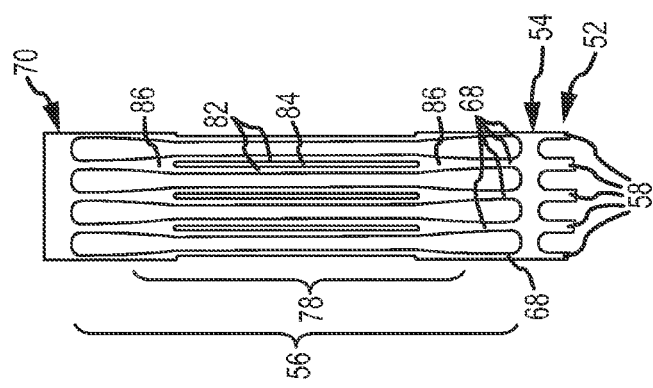
FIG. 17 is a detail view illustrating the distal section and part of the proximal section of the cut pattern of FIG. 16.
Figure 16:
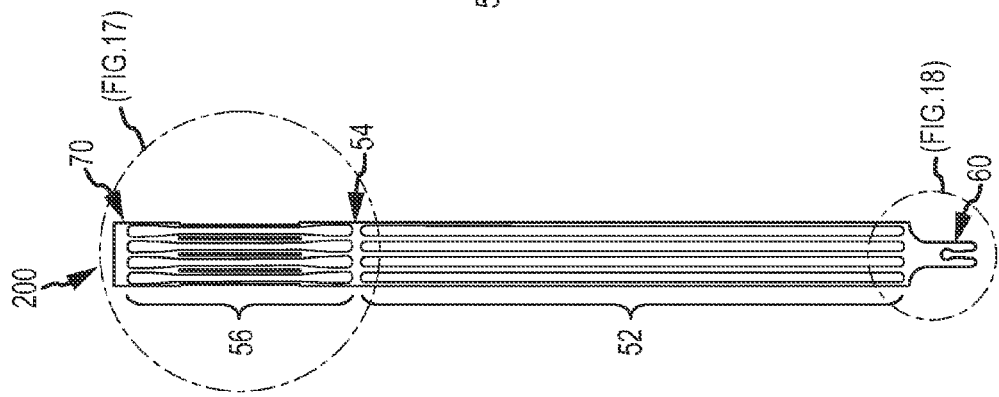
FIG. 16 illustrates a cut pattern for use in making a device similar to the device of FIG. 5, but with four struts in each of the proximal and distal sections thereof.

FIGS. 16-18 depict another example of a cut pattern 200 that can be employed (e.g., in laser cutting or etching a hypotube or sheet) to construct the device 50 of FIGS. 5-9 and 12. The cut pattern 200 of FIGS. 16-18 is suitable for a device 50 having four struts 58 in the proximal portion 52 and four struts 68 in the distal portion 56. The cut pattern 200 also forms widened portions 78 whose longitudinal midpoints are on the waist 66 of the distal portion 56, rather than on the distal face 74 thereof. Otherwise, the device 50 formed via the cut pattern 200 can be similar in structure, function and method of use to the device 50 depicted in FIGS. 5-9 and 12 and described elsewhere herein. The cut pattern 200 provides uncut areas that form the various components of the device 50. Those components of the device 50 are marked in FIGS. 16-18 with the same reference numerals as in FIGS. 5-9 and 12 (and, for common components, as in FIGS. 10-11).

FIGS. 8, 9 and 11 illustrate examples of the placement of the device 50 at a bifurcation 25. The proximal section 52 is anchored in the afferent or parent vessel 30, the intermediate section 54 allows perfusion to the branch or efferent vessels 32, 34, and the distal section 56 acts as scaffolding to inhibit herniation of embolic material from the aneurysm 20, and/or to induce thrombogenesis in the aneurysm 20.

Figure 19:
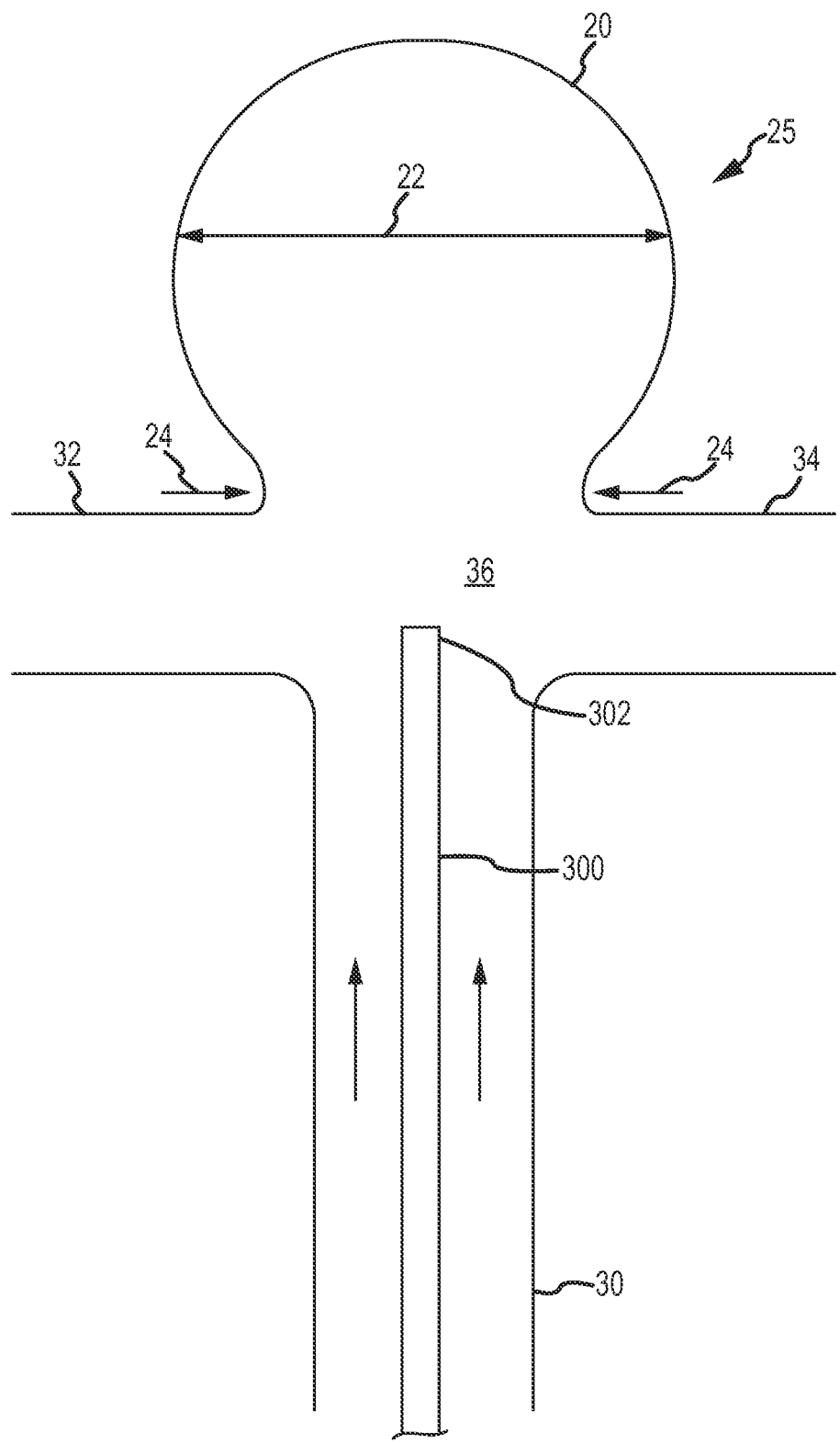
FIG. 19 illustrates part of a method of inserting a vascular remodeling device into a vascular bifurcation having an aneurysm, and/or of treating the aneurysm.
Figure 20:
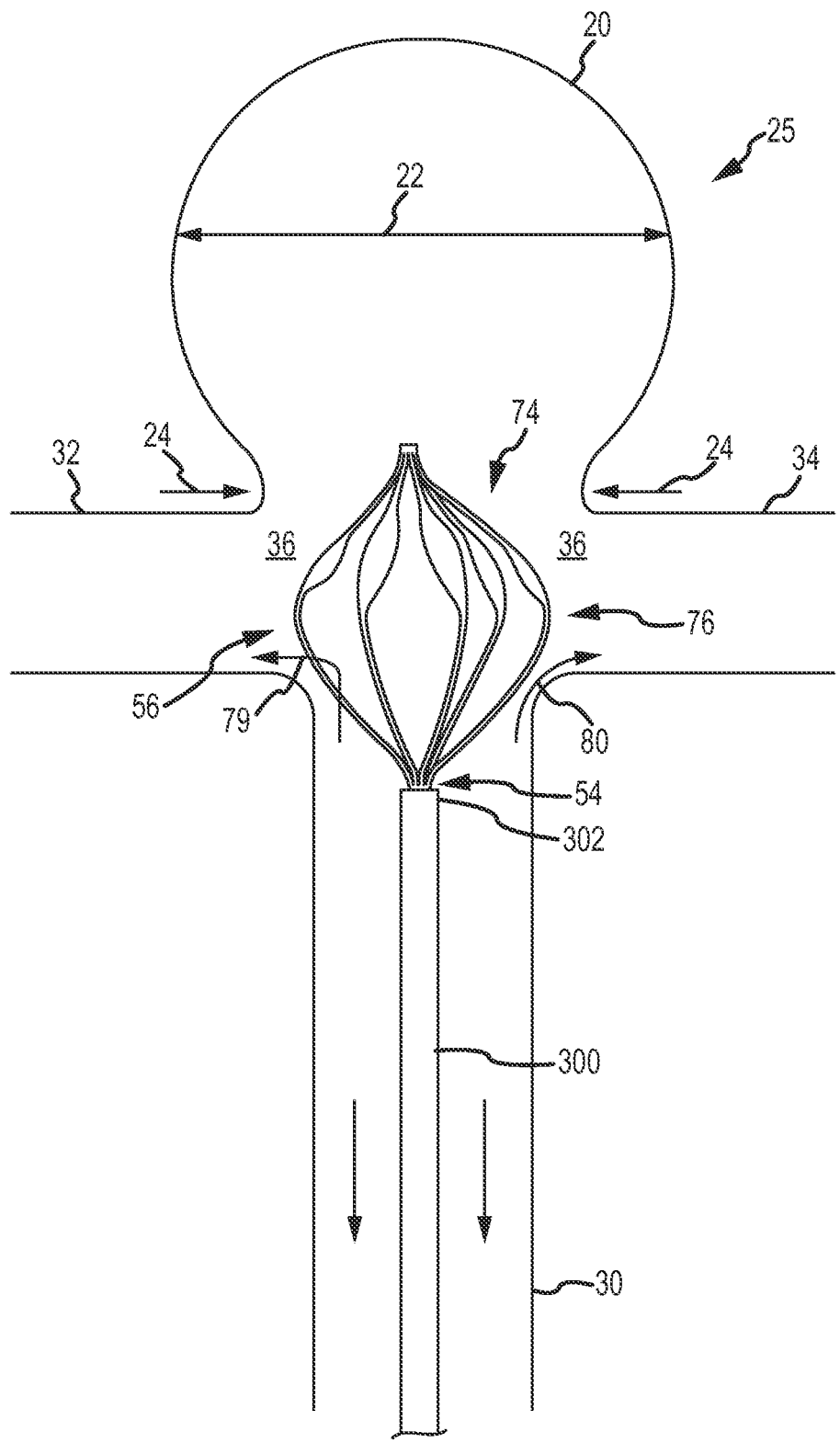
FIG. 20 illustrates another part of the method of FIG. 19.
Figure 21:
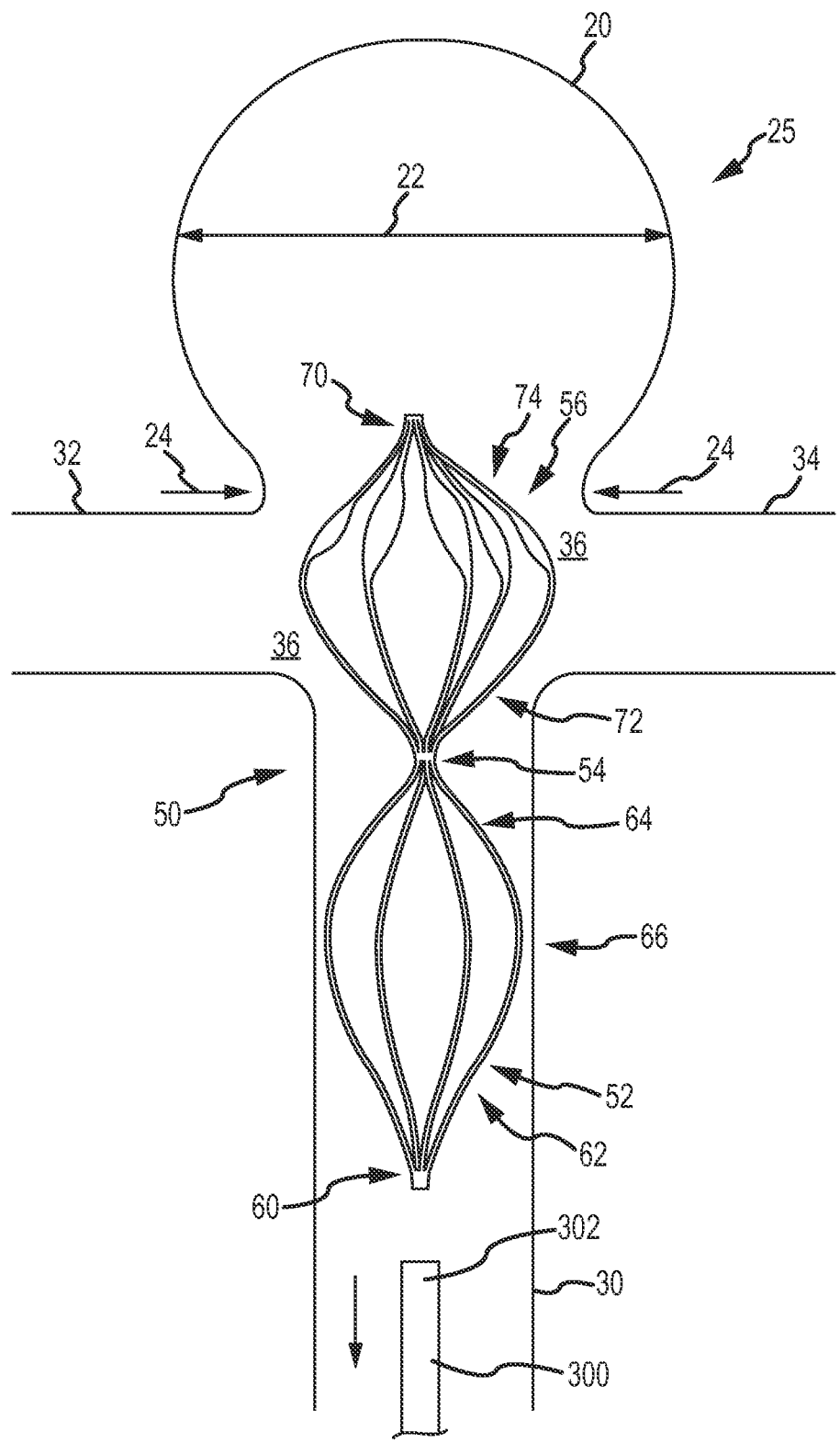
FIG. 21 illustrates another part of the method of FIGS. 19-20.

Positioning of the device 50 using the parent vessel 30 as the delivery path for the device 50 may be accomplished via, for example, the method illustrated in FIGS. 19-21. First, as shown in FIG. 19, a delivery catheter 300 (e.g., a microcatheter or other catheters that can be tracked through and reach the location of the aneurysm 20) is inserted into the patient's vasculature and advanced distally through the parent vessel 30 until a distal tip 302 of the catheter 300 is placed in the junction 36, or in the parent vessel 30 proximal of but near the junction 36, or in the aneurysm 22. The device 50 is then is inserted in the proximal end of the catheter 300 (or it may be positioned in the catheter 300 prior to placement of the distal tip 302).

As seen in FIG. 20, the distal section 56 of the device 50 is then pushed out of the distal end of the catheter 300 (e.g., using a push wire and pulling the catheter back), allowing the distal section 56 to expand (e.g., self-expand). While the proximal section 52 remains at least partially contracted within the catheter 300 as shown in FIG. 20, the position of the expanded distal section 56 relative to the junction 36, aneurysm neck 24 and parent vessel 30 can be adjusted via manipulation of the catheter 300 (and/or push wire, etc.).

One example of a desired placement of the distal section 56 is depicted in FIG. 20, in which the distal face 74 of the distal section 56 spans the aneurysm neck 24 and/or reduces the effective size of the neck. Such spanning and/or reduction can involve positioning the distal section 56 such that the distal face 74 projects into the neck 24, as depicted in FIG. 20. The placement of the distal section 56 can also involve causing the expanded waist 76 to engage the inner wall of the junction 36. Such engagement of the waist 76 (and/or other portions of the distal section 56) with the inner wall of the junction 36 can establish and/or maintain both the longitudinal (proximal-distal) and lateral (transverse to the longitudinal direction) position of the distal section 56 relative to the aneurysm neck 24.

To achieve a desired degree of engagement of the distal section 56 with the junction 36, the presently described method can include determining the size, width or diameter of the junction 36, and selecting a device 50 whose distal section 56 has an unconstrained expanded size, width or diameter (e.g. at the waist 76 thereof) which is larger than that of the junction 36. Preferably, the selected distal section 56 is somewhat larger than the junction 36, for example by about 0.5-1.0 mm.

When the distal section 56 is positioned in the junction 36 as shown in FIG. 20, the inward-tapering, minimally occlusive struts 68 of the proximal face 72 can allow blood to flow with minimal or no obstruction from the parent vessel 30 to the branch vessels 32, 34, either through the proximal face 72 (arrow 79) or around the proximal face 72 (arrow 80). At the same time, the relatively highly occlusive distal face 74 can span the neck 24 and/or reduce the effective size of the neck.

The deployment of the device 50 can further proceed with additional proximal withdrawal of the catheter 300 (and/or distal pushing of the device 50) so that the intermediate section 54 emerges from the catheter 300, followed by the proximal section 52, which is allowed to expand (e.g. self-expand). In this manner, the waist 66 can engage the inner wall of the parent vessel 30 as shown in FIG. 21, and the proximal section 52 can secure the position of the device 50, particularly against longitudinal movement. Additionally, the extension of the proximal section 52 into the parent vessel 30 can prevent rotation of the distal section 56 in the junction 36 (or, where applicable, the neck 24 or aneurysm 20), and help maintain the waist 76 in engagement with the inner wall of the junction (or neck, or aneurysm).

Where the parent vessel 30 is angled or curved with respect to the efferent vessels 32, 34 or the aneurysm 20 (see, e.g. FIG. 9), the presently described method can involve tilting, flexing or pivoting the distal section 56 relative to the proximal section 52 (or vice versa), e.g. as the device 50 is advanced into position, and/or adjusted in position or orientation once advanced and deployed or partially deployed. Where the blood vessel has a bend, the device may be a maneuvered around the bend allowing the distal section and the proximal section to pivot relative to each other at or near the intermediate section. The device 50 can be left in its tilted/flexed/pivoted configuration following deployment, as depicted in FIG. 9. When the device 50 is deployed in such angled or curved vasculature, portions of the proximal section 52 other than the waist 66 may engage the inner wall of the parent vessel 30, depending on the degree to which the sections 52, 56 are tilted with respect to each other. For example, the proximal and/or distal faces 62, 64 of the proximal section 52 may engage the inner wall of the parent vessel 30. The proximal section 52 can be tilted within the parent vessel 30 such that one side of the proximal face 62 and the opposite side of the distal face 64 both engage the inner wall of the vessel. In addition, the intermediate section 54 may engage or contact the vessel wall as well.

Where a suitable proximal end portion 60 and deployment apparatus are employed, the device 50 can be fully retrieved inside the catheter 300, the position of the catheter 300 can be adjusted, and the device 50 can be redeployed, for example to a more desirable position if the position of any section 52, 54, 56 after initial deployment of the device 50 was not as desired after initial deployment. Additionally or alternatively, the device 50 can be fully retrieved inside the catheter 300 and a different catheter or the same catheter 300 with a different device 50 (e.g., a device 50 having different dimensions such as diameter of the proximal portion 52, length of the intermediate portion 54, etc.) can be deployed, for example at a more desirable position or with more desirable properties (e.g., better anchoring, better neck coverage, etc.). Once the device 50 is positioned, the device 50 can be detached from the catheter 300, pusher wire, etc. electrolytically, mechanically, or chemically, and the catheter 300 withdrawn (see FIG. 21). The catheter 300 may then be withdrawn from the bifurcation 25, thereby leaving or permanently positioning the device 50 at the junction 36 of the bifurcation 25.

Figure 22:
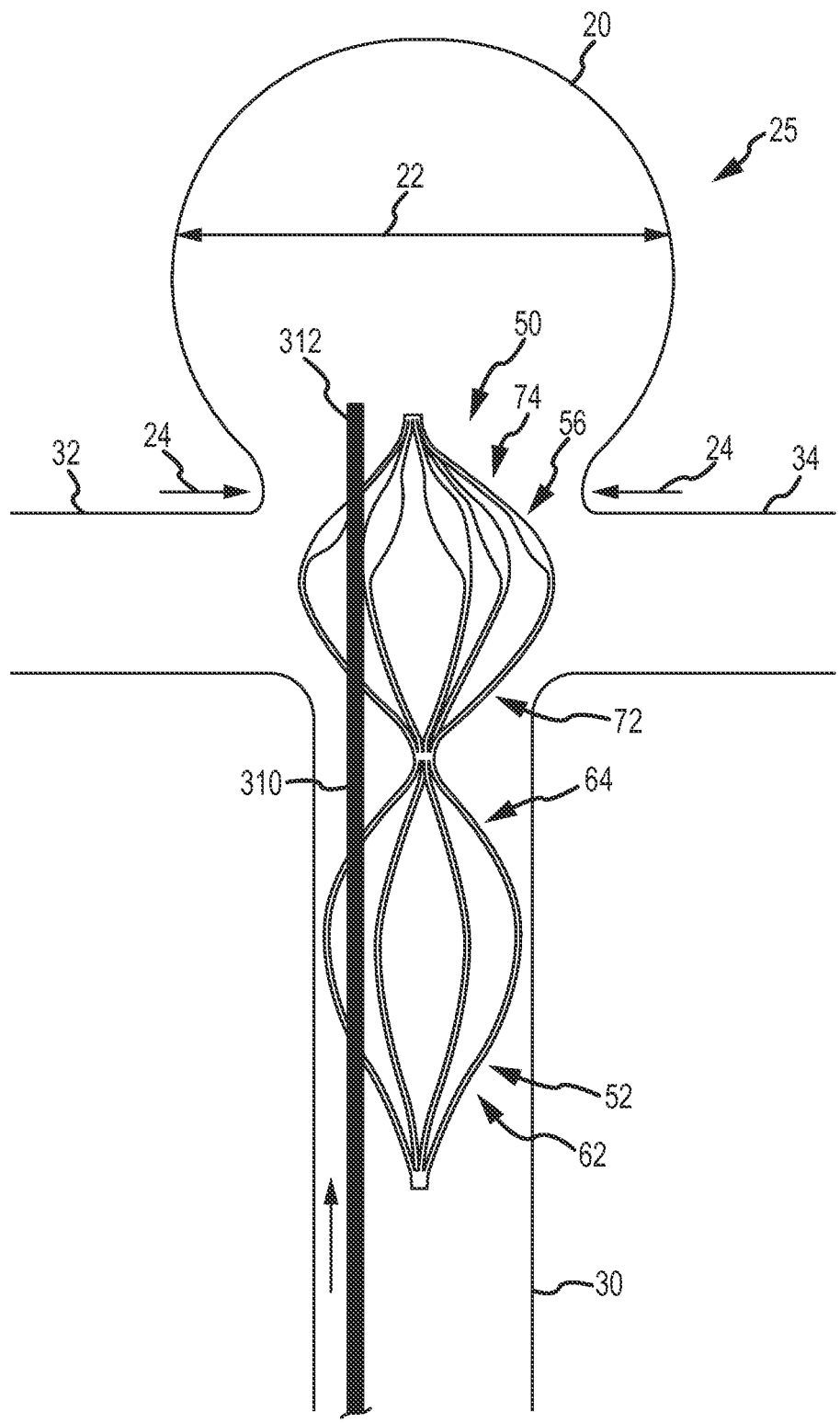
FIG. 22 illustrates part of a method of placing filling material in an aneurysm located near a bifurcation having a remodeling device therein.
Figure 23:
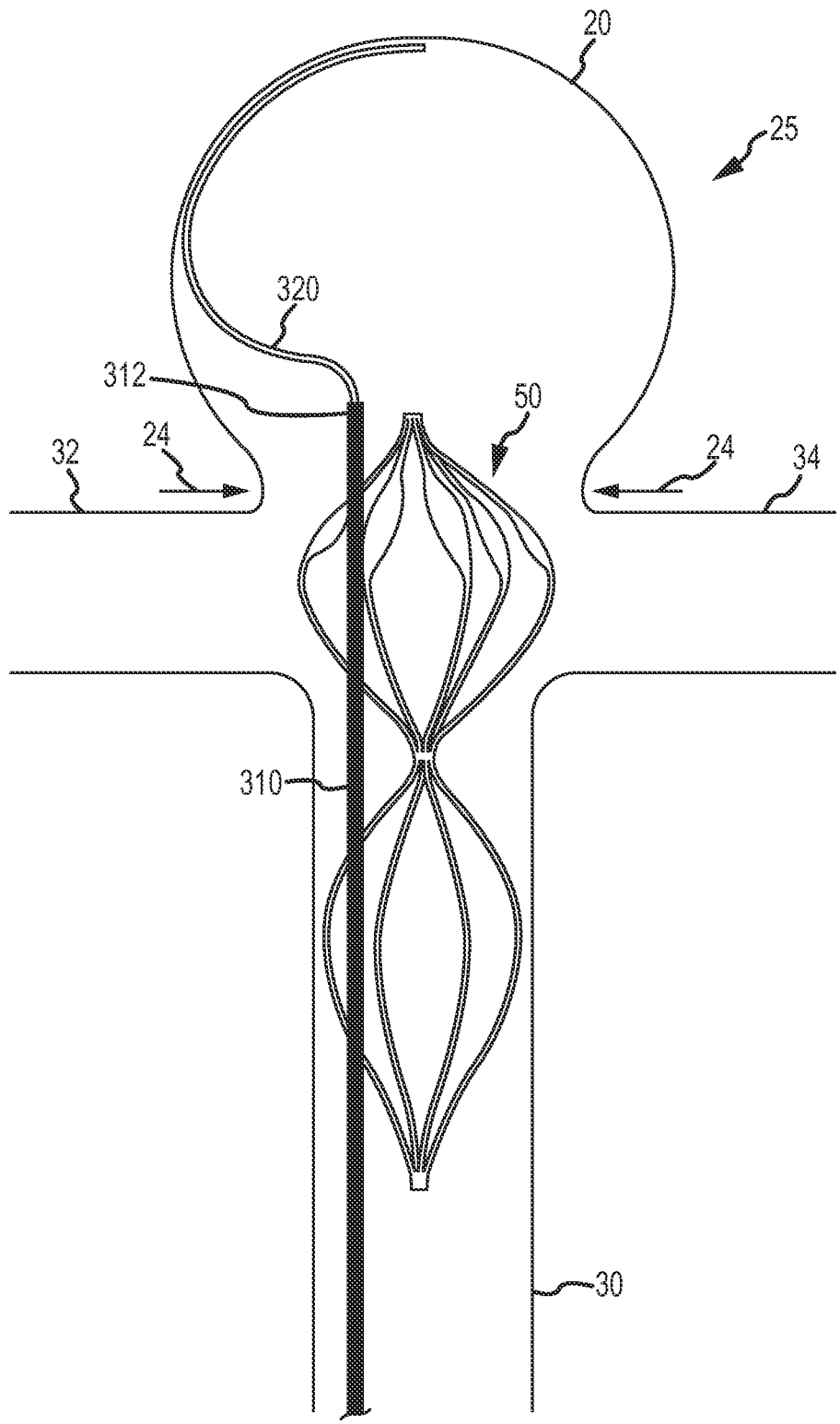
FIG. 23 illustrates another part of the method of FIG. 22.
Figure 24:
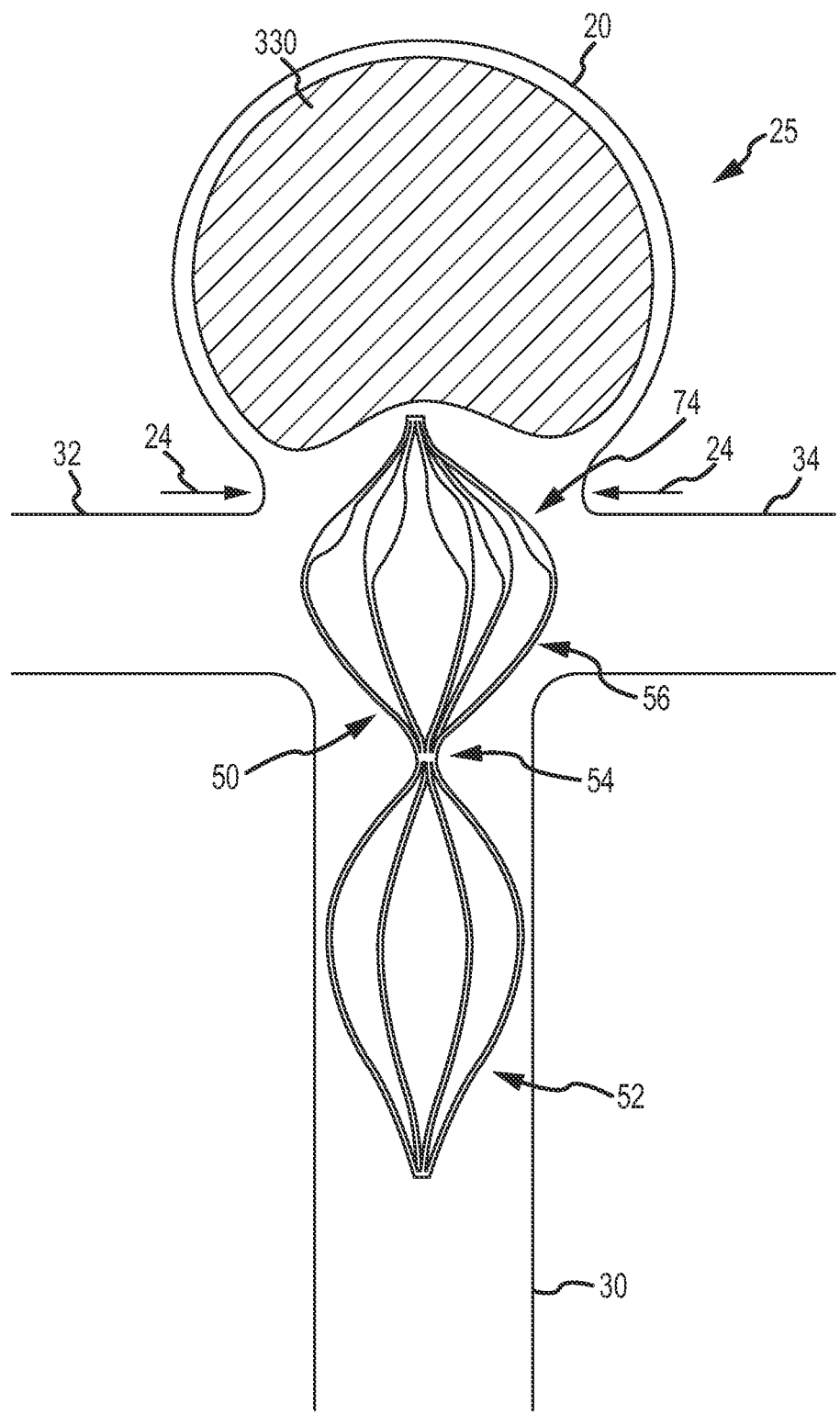
FIG. 24 illustrates another part of the method of FIGS. 22-23.
Figure 25:
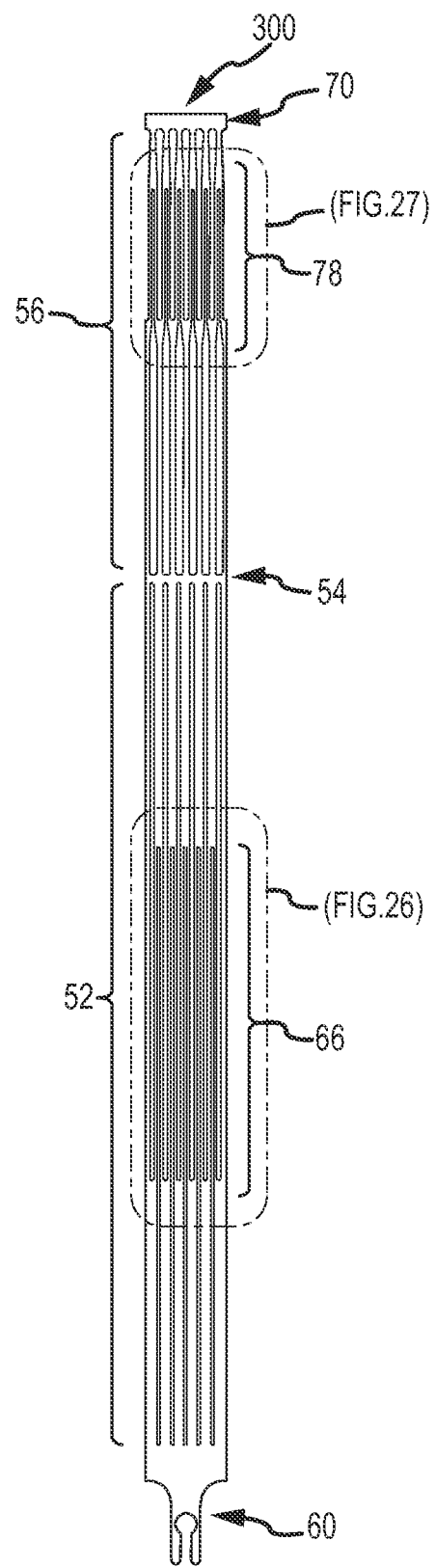
FIG. 25 illustrates a cut pattern for use in making another embodiment of the device.
Figure 26:
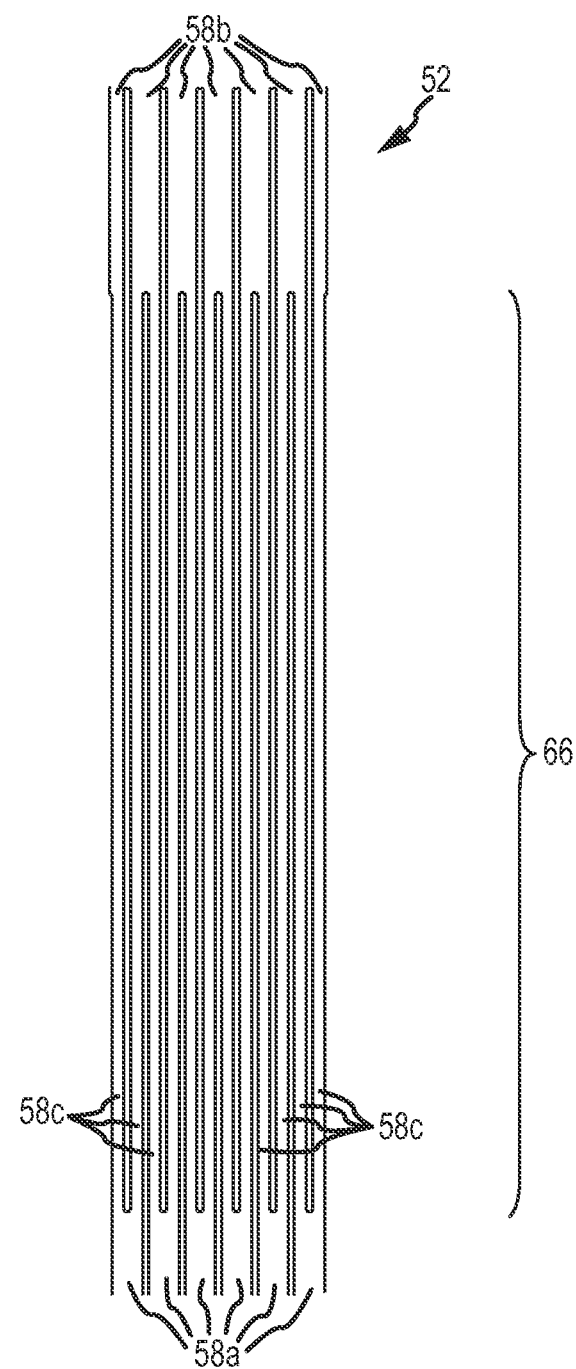
FIG. 26 illustrates a detail view of a proximal section of the cut pattern of FIG. 25.

Embolic material may be placed in the aneurysm 20 before, after, and/or during positioning of the device 50. FIGS. 22-24 depict placement of embolic material (in particular, embolic coil(s)) after placement of the device 50. A catheter, which can comprise the catheter 300 or a separate catheter 310 as shown in FIG. 22, is advanced distally through the parent vessel 30 and the proximal and distal sections 52, 56 of the device 50 until a distal tip 312 thereof passes through and is positioned distal of the distal section 56, in the fundus 22. As seen in FIG. 23, one or more coils 320 (and/or other aneurysm filling material) can then be advanced distally through the catheter 310 and into the fundus 22. Sufficient coils 320 and/or other material can be so delivered into the fundus 22 to create a mass 330 of filling material in the fundus (FIG. 24). The device 50, in particular the distal face 74 of the distal section 56, can act as a scaffolding to support the mass 330 in the aneurysm 20 and prevent herniation of coils or other material through the neck 24.

FIGS. 25-32 depict a version of the device 50 (and a cut pattern 300 for constructing it) that can be similar to any of the other versions or embodiments of the device 50 disclosed or summarized herein, in structure, configuration, function, method of manufacture, method of use, and material choice, except as further discussed herein. In the device 50 of FIGS. 25-32, the struts 58 of the proximal section 52 comprise a number (e.g. 6, as depicted, or any other suitable number) of proximal strut portions 58a and a corresponding number of distal strut portions 58b.

The proximal portions 58a and the distal portions 58b are rotated or shifted laterally with respect to each other, such that each proximal portion 58a opposes (e.g., approximately one-half of each of) two distal portions 58b, and vice versa. From the distal end of each proximal portion 58a, two sub-struts 58c extend distally to the two distal portions 58b that oppose (or are longitudinally adjacent) the proximal portion 58a from which the sub-struts 58c extend. Accordingly, each proximal portion 58a is connected to the two adjacent or opposing distal portions 58b (and vice versa) via sub-struts 58c. For example, each strut may have a proximal end, a distal end, and a center portion therebetween, the center portion connected to adjacent struts.

In another example, each strut may extend from an origination junction and be divided into a first and second branch, wherein the first branch is connected to a first adjacent strut and the second branch is connected to a second adjacent strut. In this example, a length of the first branch and a length of the second branch may be different such that a connecting point between the strut and the first adjacent strut is disposed at a different longitudinal position than a connecting point between the strut and the second adjacent strut.

According to embodiments, the length of the first branch and the length of the second branch may be the same. In another example, at least one strut may extend proximally from the intermediate section and be divided into a first and second branch at or near the waist of the proximal section. The first branch may be connected to the first adjacent strut and the second branch may be connected to the second adjacent strut. The first and second adjacent struts may extend proximally from the waist of the proximal section toward the radially central region of the device.

According to embodiments, one or more sections 52, 56 may have a first plurality of struts extending from a proximal end of the section and a second plurality of struts extending from the distal end of the section. The first and second plurality of struts may be interconnected at the waist or middle portion of the section by a third plurality of struts. Each of the first plurality of struts may be connected to two or more of the third plurality of struts. Each of the second plurality of struts may be connected to two or more of the third plurality of struts. The number of the first plurality of struts may equal the number of the second plurality of struts. The number of the third plurality of struts may be double, triple, or another multiple of one or each of the number of the first plurality of struts and the number of the second plurality of struts.

When the proximal section 52 of the device 50 of FIGS. 25-32 is expanded, the sub-struts 58c extend both longitudinally to interconnect the proximal end portion 60 and the intermediate section 54, and laterally or circumferentially to each neighboring proximal or distal portion 58a or 58b. The resulting lateral or circumferential interconnection of the struts 58 of the proximal section 52 increases the outward radial force exerted by the proximal section 52 (and the inward radial force that the proximal section 52 can withstand without collapse) when expanded and thereby improves the ability of the proximal portion 52 to "grip" the vessel wall (e.g. of the parent vessel 30) and prevent migration of the deployed device 50 along the vessel lumen. In addition, the lateral/circumferential interconnection of the struts of the proximal section 52 reduces the tendency of the expanded struts 58 to bunch together in the vessel or "half-moon." Further, the lateral/circumferential interconnection of the struts of the proximal section maintains the three dimensional shape of the proximal section. Moreover, the lateral/circumferential interconnection of the struts of the proximal section provides structural support for the interconnected struts.

As depicted in FIGS. 25-26 and 28-29, the sub-struts 58c (e.g., the peaks thereof) can form the waist 66 of the proximal portion 52, or otherwise comprise the radially outermost portion of the proximal portion 52. The sub-struts 58c can optionally be approximately longitudinally centered on the longitudinal midpoint of the proximal portion 52, such that the midpoint approximately evenly divides the sub-struts 58c in the longitudinal direction. Such an arrangement is also depicted in FIGS. 25-26 and 28-29.

Figure 27:
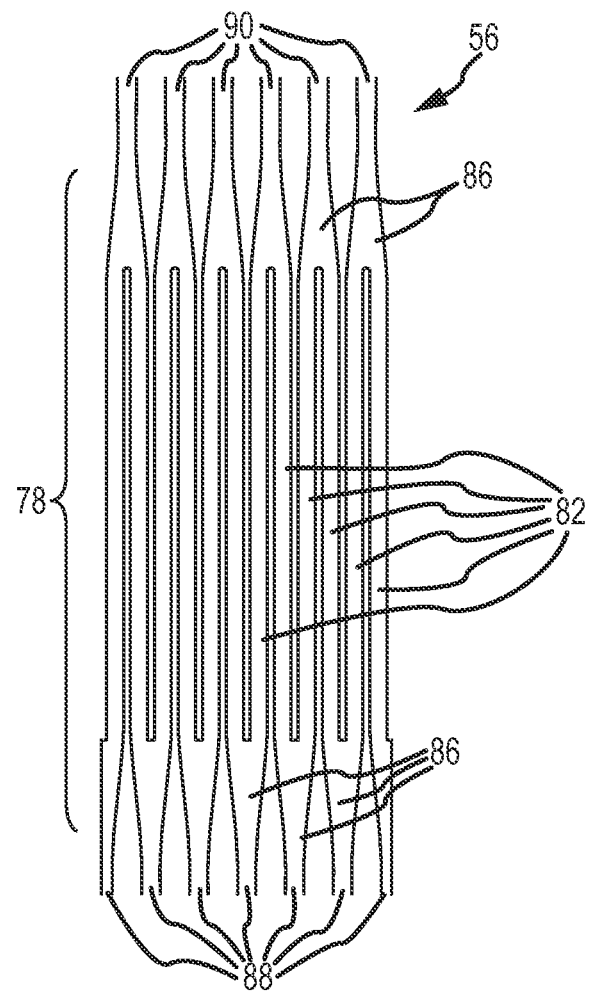
FIG. 27 illustrates a detail view of a distal section of the cut pattern of FIG. 25.
Figure 28:
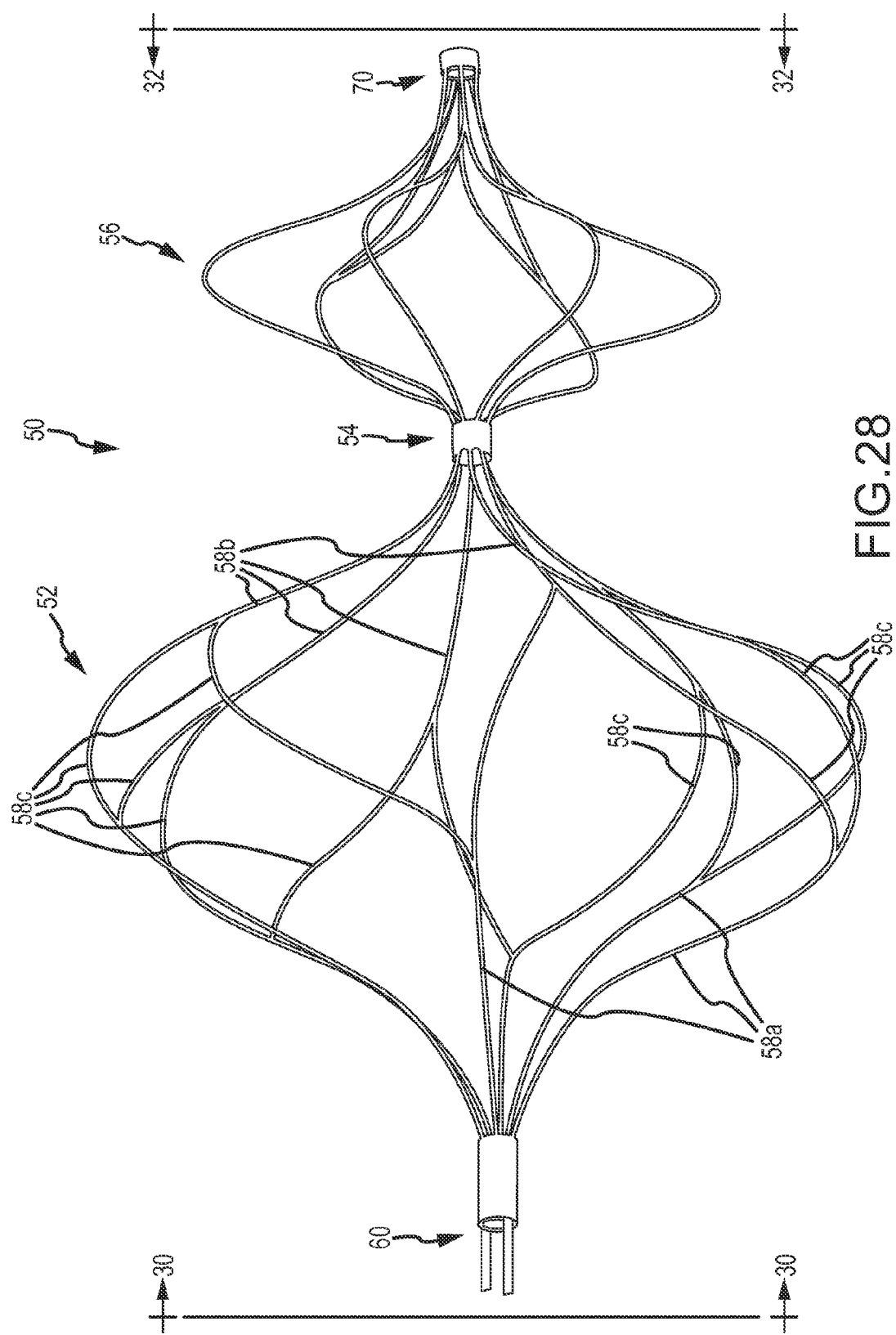
FIG. 28 illustrates a device made with the cut pattern of FIGS. 25-27, in an expanded state.
Figure 29:
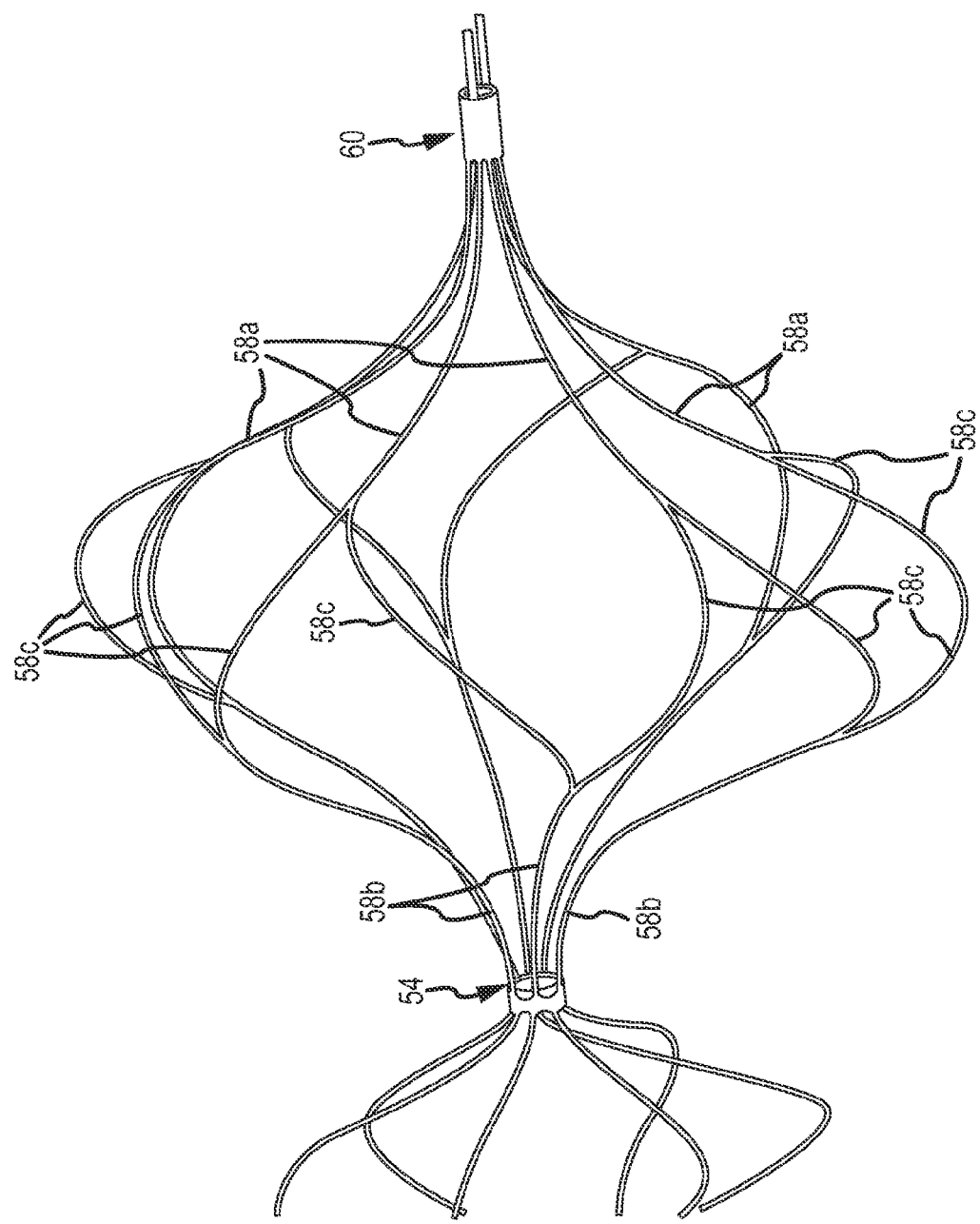
FIG. 29 illustrates a detail view of the proximal section of the device of FIG. 28.
Figure 30:
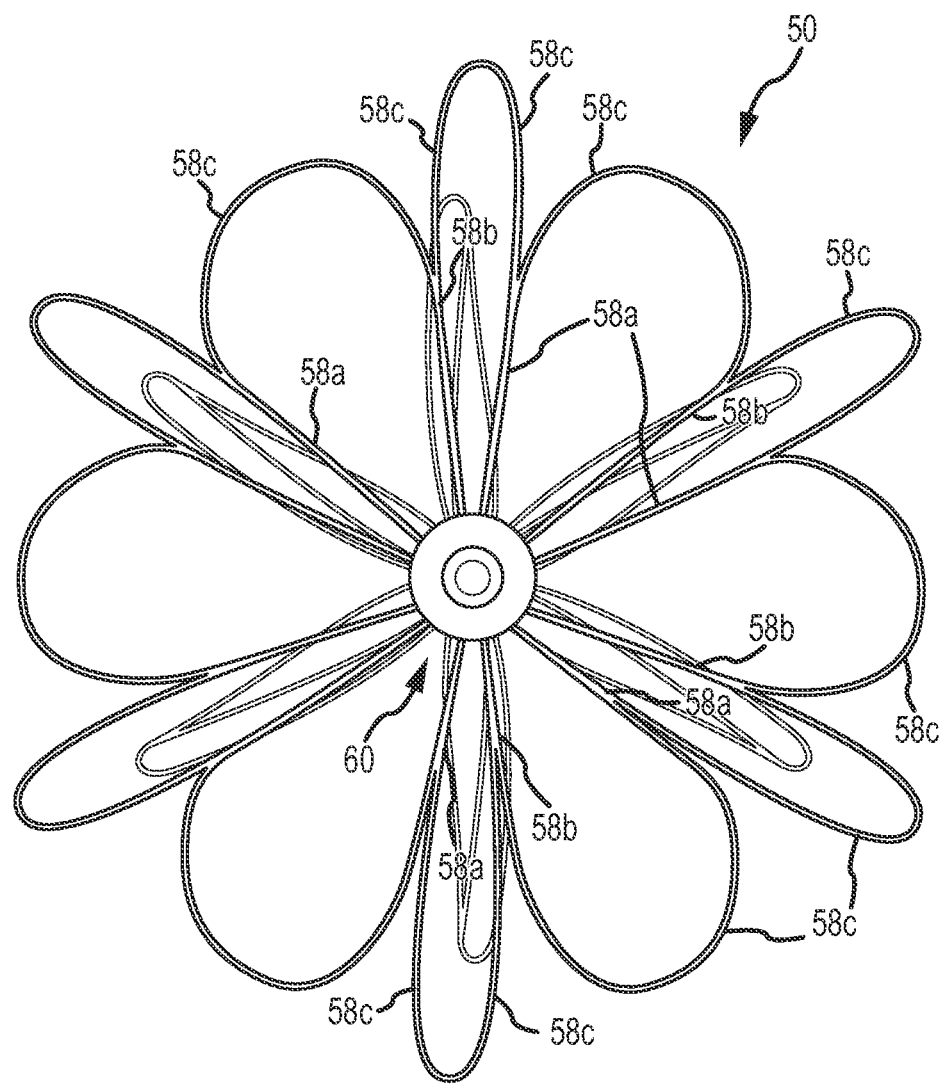
FIG. 30 illustrates a proximal end view of the proximal section of the device of FIG. 28.
Figure 31:
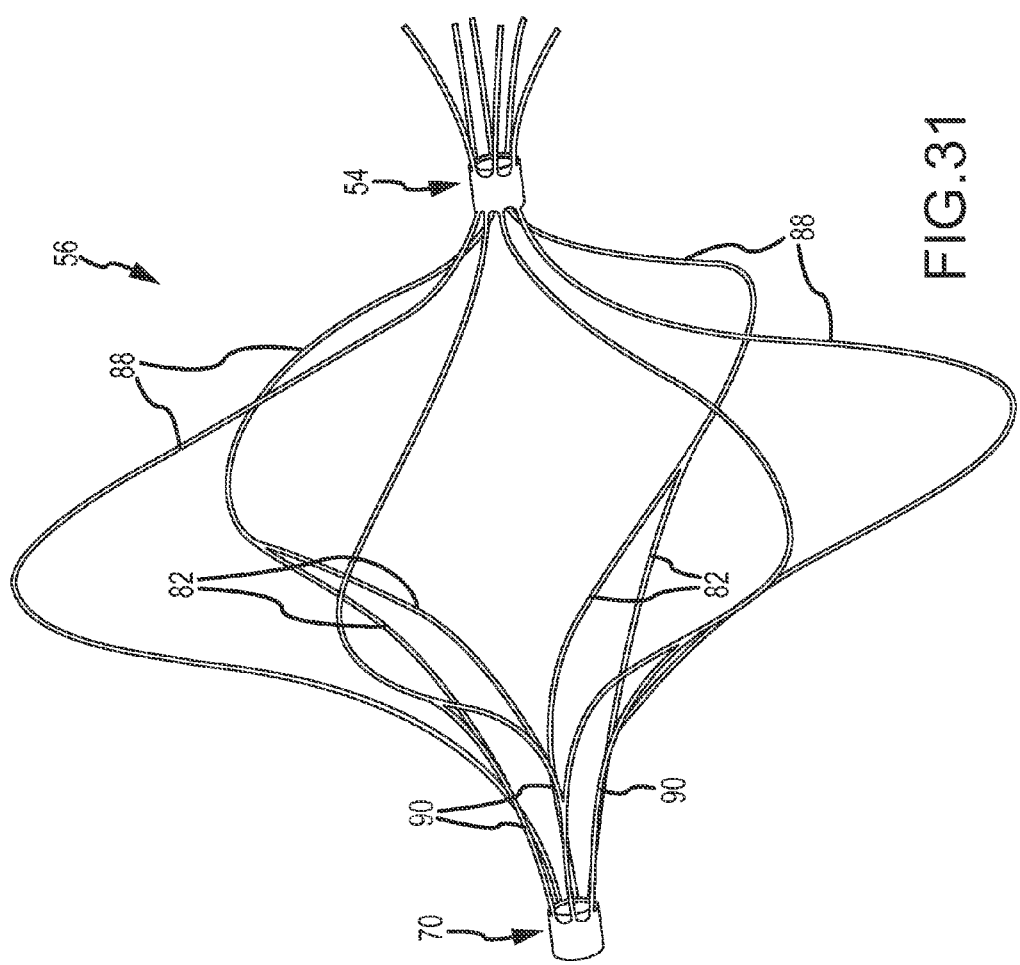
FIG. 31 illustrates a detail view of the distal section of the device of FIG. 28.
Figure 32:
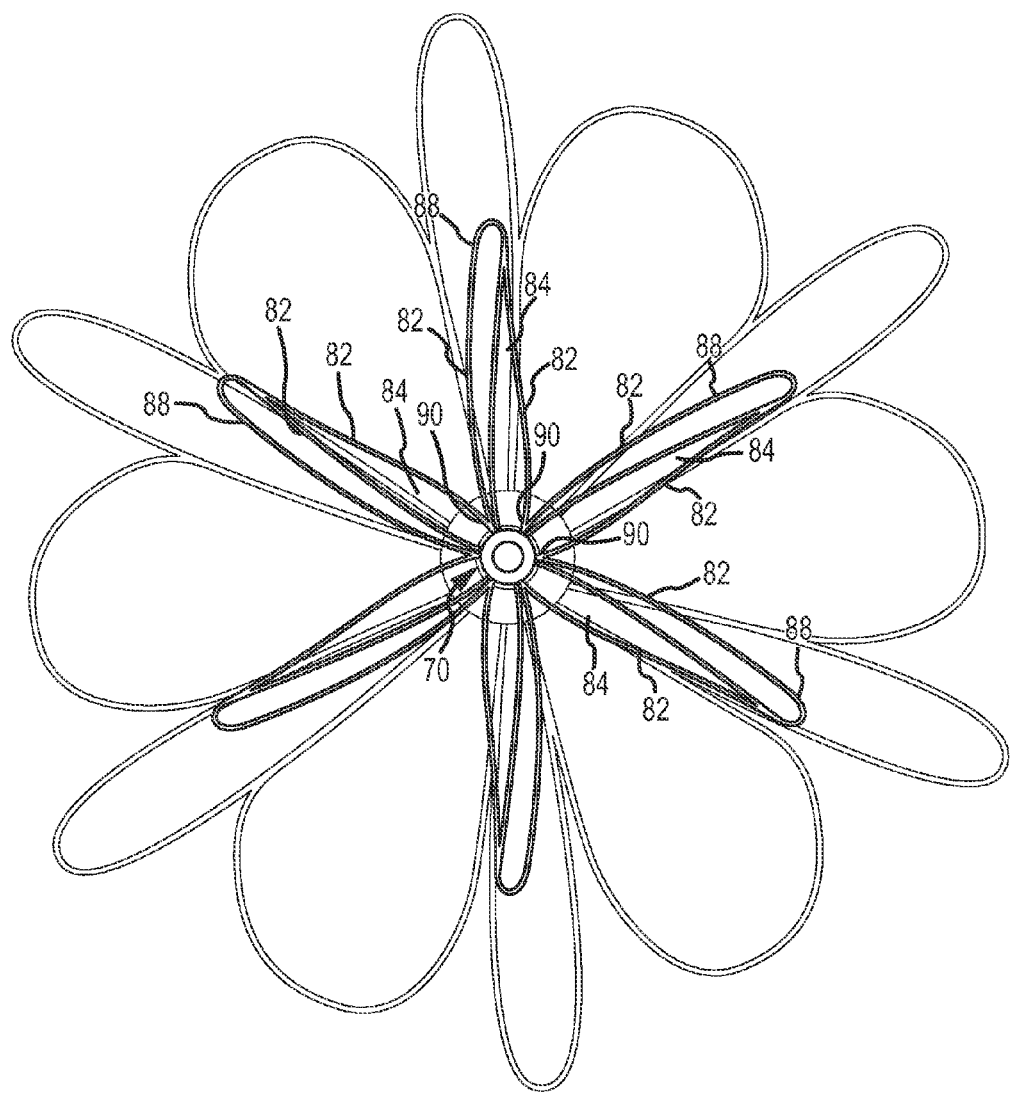
FIG. 32 illustrates a distal end view of the distal section of the device of FIG. 28.

As depicted in FIGS. 27 and 31-32, the widened portions 78 on the distal face 74 of the distal portion 56 can be formed via the lateral/circumferential interconnection arrangement employed in the proximal section 52 and discussed above. To accomplish this, the proximal strut portions 88 and distal strut portions 90 of the distal struts 68 are rotated or shifted laterally with respect to each other, such that each proximal portion 88 opposes (e.g., approximately one-half of each of) two distal portions 90, and vice versa. From the distal end of each proximal portion 88, two sub-struts 82 extend distally to the two distal portions 88 that oppose (or are longitudinally adjacent) the proximal portion 88 from which the sub-struts 82 extend. Accordingly, each proximal portion 88 is connected to the two adjacent or opposing distal portions 90 (and vice versa) via sub-struts 82. For example, at least one strut may extend distally from the intermediate section and be divided into a first and second branch at or near the waist of the distal section. The first branch may be connected to the first adjacent strut and the second branch may be connected to the second adjacent strut. The first and second adjacent struts may extend distally from the waist of the distal section toward the radially central region of the device.

When the distal section 56 of the device 50 of FIGS. 25-32 is expanded, the sub-struts 82 extend both longitudinally to interconnect the intermediate section 54 and the distal end portion 70, and laterally or circumferentially to each neighboring proximal or distal strut portion 88 or 90. Thus is formed the widened portions 78 having openings 84, in a configuration that increases the outward radial force exerted by the distal section 56 and its ability to grip the inner wall of a vessel, e.g. at the junction 36. In addition, the lateral/circumferential interconnection of the struts 68 of the distal section 56 reduces the tendency of the expanded struts 68 to bunch together in the vessel or "half-moon." Further, the lateral/circumferential interconnection of the struts of the distal section maintains the three dimensional shape of the distal section. Moreover, the lateral/circumferential interconnection of the struts of the distal section provides structural support for the interconnected struts.

As depicted in FIGS. 25, 27 and 31-32, the widened portions 78 and the sub-struts 82 can be located on the distal face 74 of the distal portion 56. The widened portions 78 and sub-struts 82 can optionally be located wholly distal of the waist 76 of the distal portion 56. Such an arrangement is also depicted in FIGS. 25-26 and 28-29. In other aspects, the widened portions may resemble the structures as disclosed elsewhere herein.

The device 50 of FIGS. 25-32 can be employed in performing any of the methods disclosed herein, e.g. any of the disclosed methods for treating aneurysms or blood vessels such as those depicted and described with reference to FIG. 8-9 or 19-24. The device 50 of FIGS. 25-32 can be deployed in vasculature, e.g. at a bifurcation, in the manner depicted in FIG. 8, 9 or 19-24. The features, components, materials or properties of the device 50 of FIGS. 25-32 can be combined with any of the features, components, materials or properties of any of the other versions or embodiments of the device 50 depicted, described or summarized herein. The configuration of one or both of the proximal and distal sections 52, 56 of the device 50 of FIGS. 25-32 can be employed when constructing the proximal and/or distal sections of any of the other versions or embodiments of the device 50 depicted, described or summarized herein.

Instead of or in addition to the placement of the mass 330 in the aneurysm 20, the device 50 can be configured as a flow diverter by making the distal face 74 of the distal section 56 sufficiently occlusive to inhibit blood flow out of the fundus 22 and promote formation of thrombus therein.

In methods in which embolic material was previously inserted in an aneurysm but has herniated, the device 50 can be used as a "rescue device" to push the herniated material back into the aneurysm and to act as a scaffolding to inhibit or prevent further herniation or prolapse of the embolic material. In certain such methods, deployment of the device 50 may advantageously avoid traversal of the junction comprising the herniated material by wires or a catheter, which may cause the herniated material to become tangled and/or dislodged and which may cause rupture of the aneurysm.

Although invention(s) have been disclosed herein in the context of certain embodiments and examples, it will be understood by those skilled in the art that the invention(s) extend beyond the specifically disclosed embodiments to other alternative embodiments and/or uses of the invention(s) and obvious modifications and equivalents thereof. In addition, while several variations of the embodiments of the invention(s) have been shown and described in detail, other modifications, which are within the scope of this disclosure, will be readily apparent to those of skill in the art based upon the present specification and drawings. It is also contemplated that various combinations or sub-combinations of the specific features and aspects of the embodiments and examples may be made and still fall within the scope of the present disclosure. It should be understood that various features and aspects of the disclosed embodiments/examples can be combined with, or substituted for, one another in order to form varying modes of the embodiments/examples of the disclosed invention(s). Thus, it is intended that the scope of the invention(s) herein disclosed should not be limited by the particular embodiments/examples described above.

What is claimed is:

1. A vascular remodeling device, comprising:
   a proximal portion radially expandable from a collapsed state to an expanded state such that, when expanded in a blood vessel, the proximal portion engages a wall of the vessel, the proximal portion having a first waist comprising a radially largest region of the proximal portion when in the expanded state;
   a distal portion radially expandable from a collapsed state to an expanded state, the distal portion having a longitudinal axis and a second waist comprising a radially largest region of the distal portion when in the expanded state, the distal portion having a distal face located distal to the second waist; and
   an intermediate portion that couples a distal end of the proximal portion and a proximal end of the distal portion, the intermediate portion comprising a radially narrowest region of the vascular remodeling device between the first and second waists of the proximal and distal portions;
   wherein the proximal portion comprises a plurality of interconnected proximal struts that extend distally from a proximal end of the proximal portion such that (a) proximal to the first waist, the proximal struts each (i) diverge from the longitudinal axis and (ii) divide into at least two proximal sub-struts; and (b) distal to the first waist, the proximal sub-struts each (i) merge with an adjacent proximal sub-strut, and (ii) converge toward the longitudinal axis, the proximal portion having a total number of proximal sub-struts that is at least double a total number of proximal struts;
   wherein the distal portion comprises, between the proximal end of the distal portion and the second waist, only a plurality of distal struts that extend distally from the proximal end of the distal portion such that (a) distal to the second waist, the distal struts each (i) diverge from the longitudinal axis and (ii) divide into at least two distal sub-struts wholly distal to the second waist; and (b) distal to the second waist, the distal sub-struts each (i) merge with an adjacent distal sub-strut, and (ii) converge toward the longitudinal axis, the distal portion having a total number of distal sub-struts that is double a total number of distal struts.

2. The vascular remodeling device of claim 1, wherein the distal struts are configured to maintain a three dimensional shape of the proximal portion.

3. The vascular remodeling device of claim 1, wherein the distal struts are configured to prevent the distal struts from aggregating toward a single side of the blood vessel.

4. The vascular remodeling device of claim 1, wherein the interconnected proximal struts are configured to structurally support each other.

5. The vascular remodeling device of claim 1, wherein each proximal strut extends from an origination junction and is divided into a first one and second one of the proximal sub-struts, wherein the first one of the proximal sub-struts is connected to a first adjacent strut and the second one of the proximal sub-struts is connected to a second adjacent strut.

6. The vascular remodeling device of claim 5, wherein a length of the first one of the proximal sub-struts and a length of the second one of the proximal sub-struts are different.

7. The vascular remodeling device of claim 5, wherein a length of the first one of the proximal sub-struts and a length of the second one of the proximal sub-struts are the same.

8. The vascular remodeling device of claim 1, wherein at least one proximal strut extends proximally from the intermediate portion and is divided into a first one and second one of the proximal sub-struts at or near the first waist of the proximal portion, the first one of the proximal sub-struts connected to a first adjacent strut and the second one of the proximal sub-struts connected to a second adjacent strut.

9. The vascular remodeling device of claim 8, wherein a length of the first one of the proximal sub-struts and a length of the second one of the proximal sub-struts are different.

10. The vascular remodeling device of claim 8, wherein a length of the first one of the proximal sub-struts and a length of the second one of the proximal sub-struts are the same.

11. The vascular remodeling device of claim 8, wherein the first and second adjacent struts extend proximally from the first waist of the proximal portion toward a radially central region of the device.

12. The vascular remodeling device of claim 1, wherein the distal struts extend longitudinally and radially inward from the first waist of the distal portion to form the distal face of the distal portion.

13. The vascular remodeling device of claim 12, wherein the distal struts forming the distal face have widened portions with increased cross-sectional widths that increase an occlusiveness of the distal face, wherein the widened portions of the distal struts are each wider than a width of at least one of a plurality of proximal struts forming a face, proximal to the first waist of the distal portion.

14. The vascular remodeling device of claim 13, wherein the widened portions of the distal struts each further comprise a first and second ramp, wherein the first ramp extends from an edge of the distal strut to an edge of the widened portion, and the second ramp extends from the edge of the widened portion to the edge of the distal strut.

15. The vascular remodeling device of claim 1, wherein the intermediate portion, the proximal portion, and the distal portion are all formed from a single sheet or tube of material.

16. The vascular remodeling device of claim 1, wherein:
   the proximal portion forms a distal face located distal to the first waist of the proximal portion;
   the distal portion forms a proximal face located proximal to the second waist of the distal portion; and
   both the distal face of the proximal portion and the proximal face of the distal portion are less occlusive than the distal face of the distal portion.

17. The vascular remodeling device of claim 16, wherein the proximal portion forms a proximal face located proximal to the first waist of the proximal portion, and the proximal face of the proximal portion is less occlusive than the distal face of the distal portion.

18. The vascular remodeling device of claim 16, wherein the distal face of the proximal portion and the proximal face of the distal portion are configured such that they allow blood flow there through.

19. The vascular remodeling device of claim 1, wherein the distal face is configured to perform a therapeutic blocking function at an aneurysm, the function comprising at least one of (a) supporting maintenance of a therapeutically effective amount and/or density of at least one filling material in the aneurysm, (b) promoting thrombogenesis, and (c) diverting flow from the aneurysm.

20. The vascular remodeling device of claim 1, wherein a lumen of the intermediate portion is filled with a radiopaque material.

21. A vascular remodeling device, comprising:
a proximal portion sized for deployment in a blood vessel, the proximal portion having a longitudinal axis and being radially expandable from a collapsed state to an expanded state, the proximal portion having a first waist comprising a radially largest region of the proximal portion when in the expanded state;
a distal portion sized and configured for deployment at a junction of two or more blood vessels;
the distal portion being radially expandable from a collapsed state to an expanded state, the distal portion comprising a second waist configured to engage a wall of the junction when the distal portion is in its expanded state, the second waist comprising the radially largest region of the distal portion when the distal portion is in its expanded state;
the distal portion comprising, between a proximal end of the distal portion and the second waist, only a plurality of distal struts, the distal portion further comprising distal sub-struts that form a distal face located distal to the second waist, the distal face configured to face an aneurysm adjacent the junction when the second waist engages the wall and the distal portion is in its expanded state, wherein, distal to the second waist, (a) the distal struts each divide into at least two distal sub-struts wholly distal to the second waist; and (b) distal to the second waist, the distal sub-struts each merge with an adjacent distal sub-strut, the distal portion having a total number of distal sub-struts that is double a total number of distal struts; and
an intermediate portion that couples the proximal portion and the distal portion;
wherein the proximal portion comprises a first plurality of interconnected proximal struts that extend distally from a proximal end of the proximal portion such that (a) proximal to the first waist, the proximal struts each (i) diverge from the longitudinal axis and (ii) divide into at least two proximal sub-struts; and (b) distal to the first waist, the proximal sub-struts each (i) merge with an adjacent proximal sub-strut, and (ii) converge toward the longitudinal axis, the proximal portion having a total number of proximal sub-struts that is at least double a total number of proximal struts.

22. The vascular remodeling device of claim 21, wherein the distal face is configured to perform a therapeutic blocking function at the aneurysm, the function comprising at least one of (a) supporting maintenance of a therapeutically effective amount and/or density of at least one filling material in the aneurysm, (b) promoting thrombogenesis, and (c) diverting flow from the aneurysm.

23. The vascular remodeling device of claim 21, wherein the proximal sub-struts each merge with the adjacent proximal sub-strut to form a second plurality of proximal struts.

24. The vascular remodeling device of claim 23, wherein the number of the first plurality of proximal struts equals the number of the second plurality of proximal struts.

25. The vascular remodeling device of claim 23, wherein the number of the proximal sub-struts is double each of the number of the first plurality of proximal struts and the number of the second plurality of proximal struts.

26. The vascular remodeling device of claim 21, wherein the interconnected proximal struts are configured to maintain a three-dimensional shape of the proximal portion.

27. The vascular remodeling device of claim 21, wherein the interconnected proximal struts are configured to prevent the proximal struts from moving substantially toward a side of the blood vessel.

28. The vascular remodeling device of claim 21, wherein the interconnected proximal struts are configured to support each other structurally.

29. The vascular remodeling device of claim 21, wherein each proximal strut extends from an origination junction and is divided into a first one and second one of the proximal sub-struts, wherein the first one of the proximal sub-struts is connected to a first adjacent strut and the second one of the proximal sub-struts is connected to a second adjacent strut.

30. The vascular remodeling device of claim 21, wherein at least one proximal strut extends proximally from the intermediate portion and is divided into a first one and second one of the proximal sub-struts at or near the first waist, the first one of the proximal sub-struts connected to a first adjacent strut and the second one of the proximal sub-struts connected to a second adjacent strut.

31. The vascular remodeling device of claim 30, wherein a length of the first one of the proximal sub-struts and a length of the second one of the proximal sub-struts are different.

32. The vascular remodeling device of claim 30, wherein a length of the first one of the proximal sub-struts and a length of the second one of the proximal sub-struts are the same.

33. The vascular remodeling device of claim 30, wherein the first and second adjacent struts extend proximally from the first waist toward a radially central region of the vascular remodeling device.

34. The vascular remodeling device of claim 21, wherein the distal struts extend longitudinally and radially inward from the second waist to form the distal face of the distal portion.

35. The vascular remodeling device of claim 34, wherein the distal struts extend distally, from a proximal end of the distal portion, substantially along a distal portion longitudinal axis; and wherein proximal to the second waist, the distal struts (i) diverge from the longitudinal axis and (ii) each divide into at least two distal sub-struts; and wherein distal to the second waist, the distal sub-struts (i) merge with an adjacent strut, and (ii) converge toward the longitudinal axis.

36. The vascular remodeling device of claim 34, wherein the distal struts are configured to maintain a three dimensional shape of the distal portion.

37. The vascular remodeling device of claim 34, wherein the distal struts are configured to prevent the distal struts of the distal portion from moving to a side of the blood vessel.

38. The vascular remodeling device of claim 34, wherein the distal struts are configured to structurally support each other.

39. The vascular remodeling device of claim 21, wherein each distal strut extends from an origination junction and is divided into a first one and second one of the distal sub-struts, wherein the first one of the distal sub-struts is connected to a first adjacent distal strut and the second one of the distal sub-struts is connected to a second adjacent distal strut.

40. The vascular remodeling device of claim 21, wherein at least one distal strut extends distally from the intermediate portion and is divided into a first one and second one of the distal sub-struts at or near the second waist, the first one of the distal sub-struts connected to a first adjacent distal strut and the second one of the distal sub-struts connected to a second adjacent distal strut.

41. The vascular remodeling device of claim 21, wherein:
the proximal portion forms a distal face located distal to the first waist;
the distal portion forms a proximal face located proximal to the second waist; and both the distal face of the proximal portion and the proximal face of the distal portion are less occlusive than the distal face of the distal portion.

42. The vascular remodeling device of claim 21, wherein a lumen of the intermediate portion is filled with a radiopaque material.

* * * * *